United States Patent
Tomizawa et al.

(10) Patent No.: US 11,864,875 B2
(45) Date of Patent: Jan. 9, 2024

(54) DATA ANALYSIS DEVICE

(71) Applicant: SHARP KABUSHIKI KAISHA, Sakai (JP)

(72) Inventors: Ryota Tomizawa, Sakai (JP); Yoshihisa Adachi, Sakai (JP); Yuki Edo, Sakai (JP); Rieko Ogawa, Sakai (JP)

(73) Assignee: SHARP KABUSHIKI KAISHA, Sakai (JP)

(*) Notice: Subject to any disclaimer, the term of this patent is extended or adjusted under 35 U.S.C. 154(b) by 564 days.

(21) Appl. No.: 17/049,753

(22) PCT Filed: Apr. 18, 2019

(86) PCT No.: PCT/JP2019/016627
§ 371 (c)(1),
(2) Date: Oct. 22, 2020

(87) PCT Pub. No.: WO2019/208388
PCT Pub. Date: Oct. 31, 2019

(65) Prior Publication Data
US 2021/0248739 A1    Aug. 12, 2021

(30) Foreign Application Priority Data

Apr. 23, 2018 (JP) ................. 2018-082301

(51) Int. Cl.
*G06K 9/00* (2022.01)
*A61B 5/024* (2006.01)
(Continued)

(52) U.S. Cl.
CPC ........ *A61B 5/02416* (2013.01); *G06T 7/0012* (2013.01); *G06T 7/90* (2017.01);
(Continued)

(58) Field of Classification Search
None
See application file for complete search history.

(56) References Cited

U.S. PATENT DOCUMENTS

| | | | |
|---|---|---|---|
| 2013/0204143 A1 | 8/2013 | Narusawa | |
| 2016/0007865 A1 | 1/2016 | Sakata et al. | |
| 2018/0085010 A1 | 3/2018 | Jones et al. | |

FOREIGN PATENT DOCUMENTS

| | | |
|---|---|---|
| JP | 2013-176535 A | 9/2013 |
| JP | 2016-193021 A | 11/2016 |

(Continued)

*Primary Examiner* — Wei Wen Yang
(74) *Attorney, Agent, or Firm* — ScienBiziP, P.C.

(57) ABSTRACT

A possibility of extracting a signal less affected by a variation factor is increased. A data analysis device includes a data extraction unit, that extracts, as extracted data, a plurality of primary characteristic values corresponding to a plurality of extraction conditions which are different from each other and secondary characteristic values corresponding to the plurality of primary characteristic values, for each of a plurality of pieces of input data, a data identification unit that performs predetermined analysis processing on a plurality of pieces of extracted data, and identifies, based on a result of the predetermined analysis processing, analysis target data, and a data output unit that outputs output data generated based on a plurality of pieces of analysis target data.

16 Claims, 16 Drawing Sheets

(51) Int. Cl.
*G06T 7/90* (2017.01)
*G16H 10/40* (2018.01)
*G16H 50/70* (2018.01)
*G06T 7/00* (2017.01)
*G10L 25/51* (2013.01)
*H04R 1/08* (2006.01)
*G06V 10/56* (2022.01)
*G06V 10/77* (2022.01)
*G06V 40/70* (2022.01)
*G06V 40/10* (2022.01)

(52) U.S. Cl.
CPC ......... *G06V 10/56* (2022.01); *G06V 10/7715* (2022.01); *G06V 40/70* (2022.01); *G10L 25/51* (2013.01); *G16H 10/40* (2018.01); *G16H 50/70* (2018.01); *H04R 1/08* (2013.01); *G06T 2207/10024* (2013.01); *G06T 2207/20076* (2013.01); *G06T 2207/30004* (2013.01); *G06V 40/15* (2022.01)

(56) References Cited

FOREIGN PATENT DOCUMENTS

| JP | 2017153963 A | * | 9/2017 | ............... A61B 5/00 |
|----|--------------|---|--------|---------------------------|
| WO | 2014/155750 A1 | | 10/2014 | |
| WO | 2016/163019 A1 | | 10/2016 | |

* cited by examiner

| POSITION | 0 | 1 | 2 | 3 | ... |
|---|---|---|---|---|---|
| SIGNAL Si1 | 100 | 110 | 120 | 110 | ... |
| SIGNAL Si2 | 80 | 100 | 120 | 90 | ... |
| SIGNAL Si3 | 40 | 50 | 45 | 50 | ... |

(b)

| No. | 1 | 2 | 3 | ... |
|---|---|---|---|---|
| ANSWER OF A | I | II | III | ... |
| ANSWER OF B | I |  | IV | ... |

(c)

| TIME | 0 | 10 | 20 | 30 | ... |
|---|---|---|---|---|---|
| STRENGTH St1 | 5 | 6 | 4 | 3 | ... |

| TIME | 0 | 15 | 30 | 45 | ... |
|---|---|---|---|---|---|
| STRENGTH St2 | 4 | 5 | 2 | 6 | ... |

| TIME | 5 | 25 | 45 | 65 | ... |
|---|---|---|---|---|---|
| STRENGTH St3 | 8 | 10 | 9 | 12 | ... |

FIG.3

SET IN OF INPUT DATA

INPUT DATA D1

| M | 0 | 1 | 2 | 3 | 4 | 5 |
|---|---|---|---|---|---|---|
| Si1 | 5 | 8 | 7 | 6 | 4 | 8 |

INPUT DATA D2

| M | 0 | 1 | 2 | 3 | 4 | 5 |
|---|---|---|---|---|---|---|
| Si2 | 5 | 4 | 6 | 10 | 7 | 5 |

INPUT DATA D3

| M | 0 | 1 | 2 | 3 | 4 | 5 |
|---|---|---|---|---|---|---|
| Si3 | 6 | 7 | 3 | 2 | 5 | 0 |

SET DS1 OF EXTRACTED DATA

EXTRACTED DATA D11

| M | 1 | 2 | 5 |
|---|---|---|---|
| Si1 | 8 | 7 | 8 |

EXTRACTED DATA D12

| M | 1 | 2 | 5 |
|---|---|---|---|
| Si2 | 4 | 6 | 5 |

EXTRACTED DATA D13

| M | 1 | 2 | 5 |
|---|---|---|---|
| Si3 | 7 | 3 | 0 |

EXTRACTION CONDITION

| C1 | M=1, 2, 5 |
| C2 | M=0, 1, 2, 3 |
| C3 | M=1, 4 |
| C4 | M=0, 1, 2, 3, 4, 5 |

FIG.4

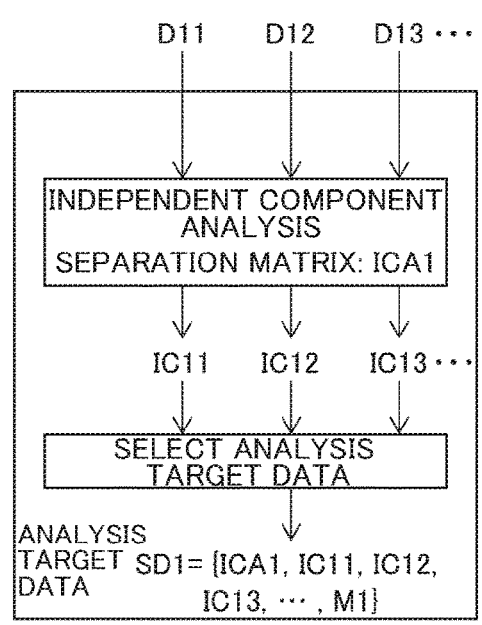

(a)

D11  D12  D13···
↓    ↓    ↓
INDEPENDENT COMPONENT ANALYSIS
SEPARATION MATRIX: ICA1
↓    ↓    ↓
IC11  IC12  IC13···
↓    ↓    ↓
SELECT ANALYSIS TARGET DATA
↓
ANALYSIS TARGET DATA  SD1= {ICA1, IC11, IC12, IC13, ···, M1}

(b)

| EXTRACTION CONDITION | ANALYSIS TARGET DATA |
|---|---|
| C1 | SD1 |
| C2 | SD2 |
| C3 | SD3 |
| ⋮ | ⋮ |

FIG.9
ANALYSIS TARGET CANDIDATE DATA IC1a
IC11a
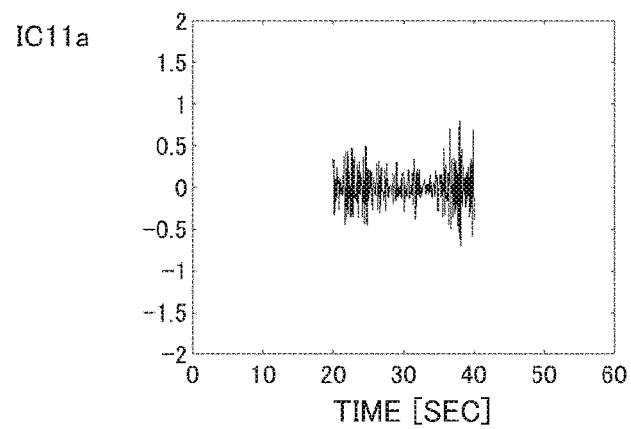
IC12a
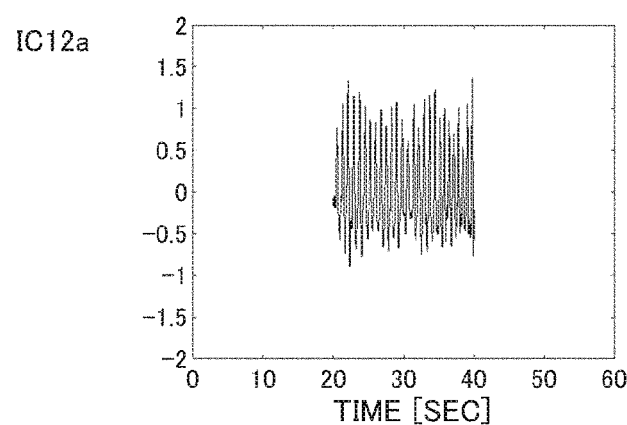
IC13a
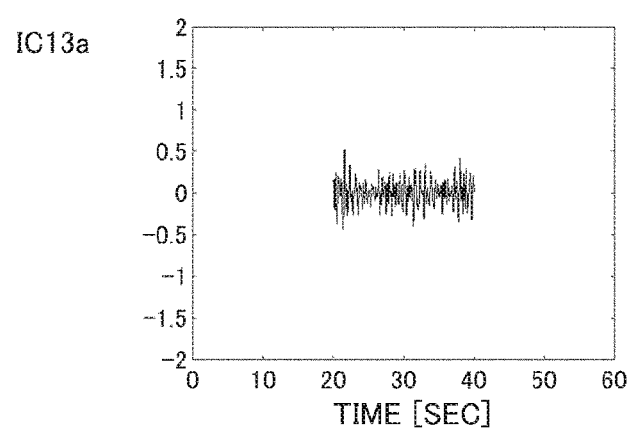

FIG.10
ANALYSIS TARGET DATA  SDa
SD1a
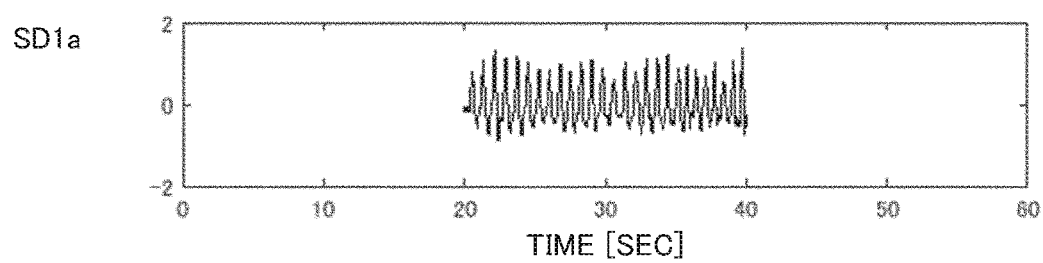
SD2a
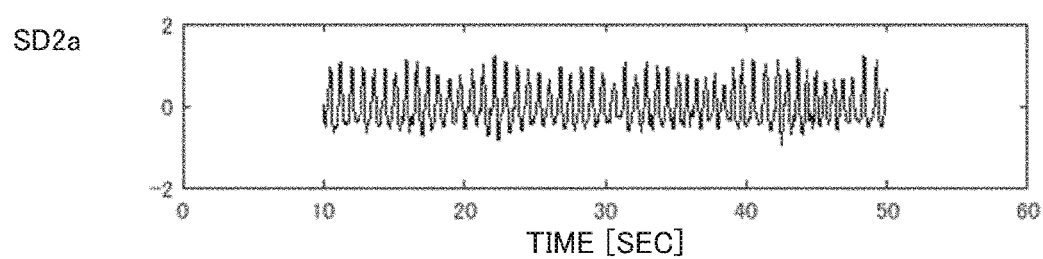
SD3a
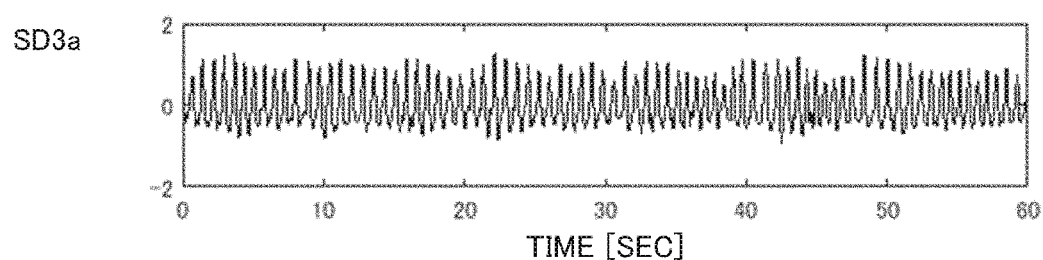

FIG.12
ANALYSIS TARGET DATA  SDb
SD1b
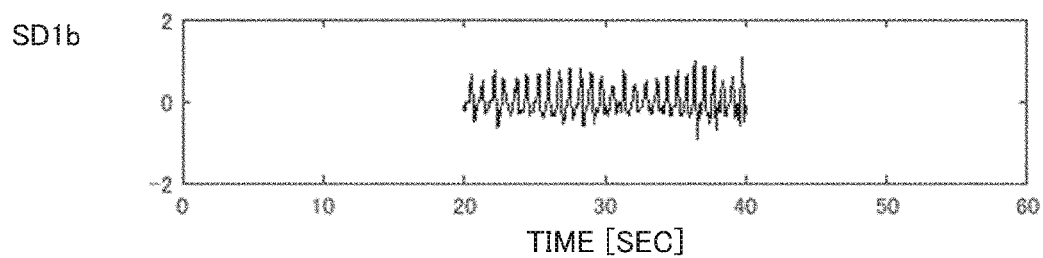
SD2b
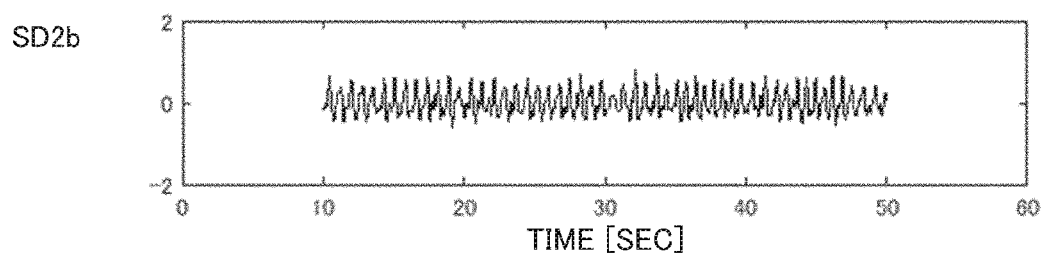
SD3b
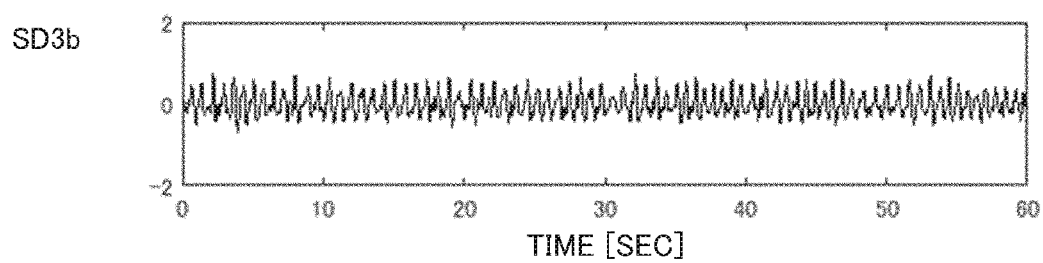

DATA ANALYSIS DEVICE

TECHNICAL FIELD

The present disclosure relates to a data analysis device.

BACKGROUND ART

In a device for measuring a pulse wave, a technique for reducing the influence of noise caused by the movement of a measurement part or the like is disclosed in PTL 1, for example. In the technique of PTL 1, independent component analysis is performed on measurement signals output from a plurality of light receiving elements to calculate a weighting coefficient of each component when each measurement signal is separated into a plurality of components. In the technique, further, a variation of the calculated weighting coefficient is calculated for each component, the component with the smallest variation calculated is identified, and pulse wave information indicating the pulse wave is generated on the basis of the identified component.

CITATION LIST

Patent Literature

PTL 1: Japanese Unexamined Patent Application Publication No. 2013-176535 (Published Sep. 9, 2013)

SUMMARY OF INVENTION

Technical Problem

However, the technique of PTL 1 is not a technique that generates the pulse wave information on the basis of a measurement signal obtained by extracting a portion of each of the plurality of measurement signals. Therefore, in the technique of PTL 1, there is a possibility that the pulse wave information is generated on the basis of a measurement signal including a variation factor (for example, noise) which may affect results of analysis processing (for example, independent component analysis) on the measurement signal. In this case, the reliability of the pulse wave information may be reduced.

An object of one aspect of the present disclosure is to implement a data analysis device in which, even when a variation factor which may affect results of analysis processing on a signal to be analyzed is included in the signal, a possibility of extracting the signal less affected by the variation factor is increased.

Solution to Problem

In order to solve the above problem, according to one aspect of the present disclosure, there is provided a data analysis device that performs an analysis on a set of input data in which a primary characteristic value that is a characteristic value of a primary attribute is associated with a secondary characteristic value that is a characteristic value of a secondary attribute, the secondary characteristic value corresponding to the primary characteristic value.

The set of input data includes a plurality of pieces of input data in which attributes of the secondary characteristic value corresponding to the primary characteristic value are different from each other, and the data analysis device includes: a data extraction unit that extracts, as extracted data, a plurality of primary characteristic values corresponding to a plurality of extraction conditions which are different from each other and a plurality of secondary characteristic values corresponding to the plurality of primary characteristic values, for each of the plurality of pieces of input data; a data identification unit that performs predetermined analysis processing on a plurality of pieces of extracted data, and identifies, based on a result of the predetermined analysis processing, analysis target data to be analyzed; and a data output unit that outputs output data generated based on a plurality of pieces of analysis target data identified for each of the plurality of extraction conditions.

Advantageous Effects of Invention

With the data analysis device according to one aspect of the present disclosure, even when a variation factor which may affect results of analysis processing on a signal to be analyzed is included in the signal, the possibility of extracting the signal less affected by the variation factor can be increased.

BRIEF DESCRIPTION OF DRAWINGS

FIGS. 2(a) to 2(c) are diagrams showing an example of input data.

FIG. 3 is a diagram showing an example of processing of a data extraction unit included in the data analysis device.

FIG. 4(a) is a diagram showing an example of processing of a data identification unit included in the data analysis device, and FIG. 4(b) is a diagram showing an example of analysis target data stored in a storage unit included in the data analysis device.

FIG. 9 is a diagram showing an example of analysis target candidate data acquired by performing independent component analysis on the extracted data of FIG. 8.

FIG. 10 is a diagram showing an example of analysis target data corresponding to each of a plurality of extraction conditions.

FIG. 12 is a diagram showing an example of analysis target data corresponding to each of a plurality of extraction conditions.

DESCRIPTION OF EMBODIMENTS

Embodiment 1

Hereinafter, one embodiment of the present disclosure will be described in detail.

<Data Analysis Device>

Figure 1:
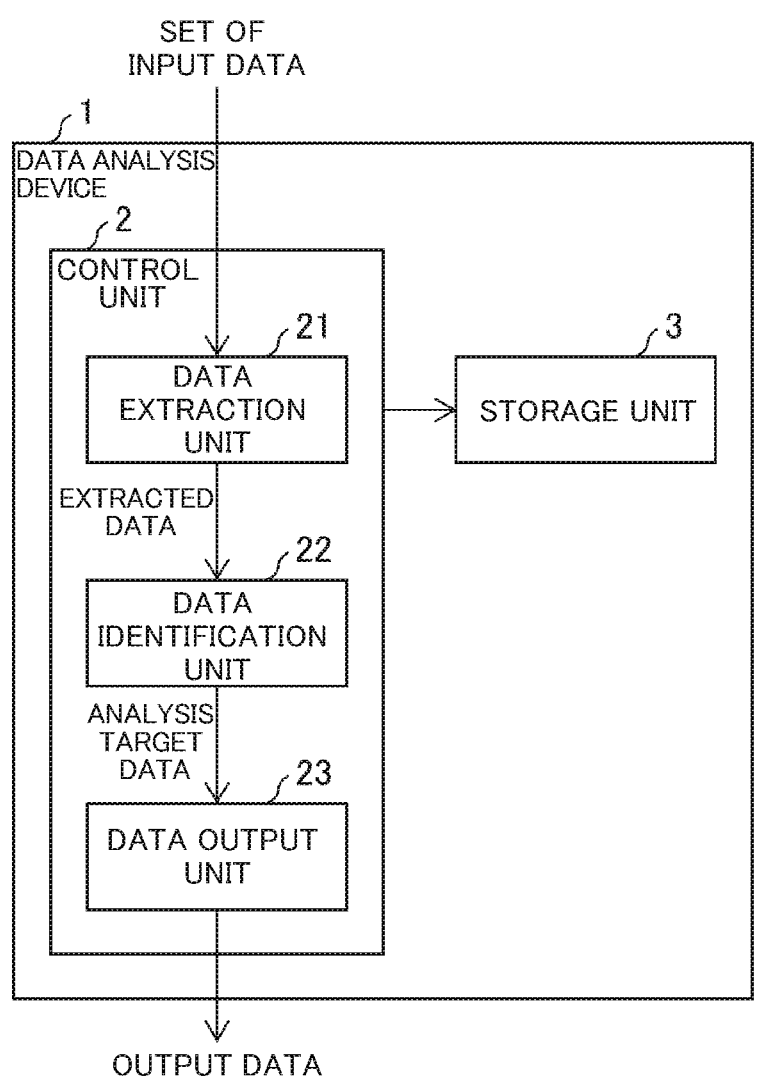
FIG. 1 is a block diagram showing an example of a data analysis device according to Embodiment 1.

FIG. 1 is a block diagram showing an example of a data analysis device 1. The data analysis device 1 performs an analysis on a set of input data in which a primary characteristic value that is a characteristic value of a primary attribute is associated with a secondary characteristic value that is a characteristic value of a secondary attribute, the secondary characteristic value corresponding to the primary characteristic value, and includes a control unit 2 and a storage unit 3 as shown in FIG. 1. The control unit 2 centrally controls the data analysis device 1, and in the present embodiment, in particular, includes a data extraction unit 21 (extraction device), a data identification unit 22 (separation device), and a data output unit 23 (output device). The storage unit 3 (memory device) stores programs processed by the control unit 2, extraction conditions (described below), analysis target data (described below), and the like.

The data extraction unit 21 extracts extracted data from the received input data. Specifically, the data extraction unit 21 extracts for each extraction condition, as extracted data, a plurality of primary characteristic values corresponding to a plurality of extraction conditions which are different from each other and a secondary characteristic value corresponding to each of the plurality of primary characteristic values, for each of a plurality of pieces of input data.

The data identification unit 22 separates desired information from a plurality of pieces of extracted data as separated data. The desired information refers to data required when the data output unit 23 generates output data.

Specifically, the data identification unit 22 performs predetermined analysis processing on the plurality of pieces of extracted data for each of the plurality of extraction conditions, and identifies analysis target data to be analyzed on the basis of a result of the analysis processing.

For example, the data identification unit 22 performs predetermined analysis processing on the plurality of pieces of extracted data for each of the plurality of extraction conditions to acquire a plurality of pieces of analysis target candidate data (separated data) that can be analyzed. The data identification unit 22 identifies the analysis target candidate data to be included in the analysis target data from the plurality of pieces of acquired analysis target candidate data. However, the data identification unit 22 may identify data related to the analysis target candidate data selected from the plurality of pieces of acquired analysis target candidate data as the data to be included in the analysis target data. Examples of the data related to the selected analysis target candidate data include a signal to noise (S/N) ratio of the analysis target candidate data, or an analysis condition used in predetermined analysis processing (for example, a separation matrix or an orthogonal matrix).

Examples of the predetermined analysis processing include independent component analysis (processing that applies a separation matrix to input data). Since independent component analysis is a generally well-known analysis processing method, by using the independent component analysis, analysis target data can be identified by a simple method. Further, the versatility of the data analysis device 1 can be improved. In addition, examples of the predetermined analysis processing include a principal component analysis, a singular value decomposition, and the like.

The data output unit 23 generates output data on the basis of the analysis target data and outputs the generated output data. The output data refers to data that is estimated (probable) to have high reliability as data to be analyzed by the data analysis device 1 or an output destination (for example, measuring device (described below)). For example, in Embodiment 2, the reliability that serves as an index for determining whether or not acquired pulse wave data is accurate pulse wave data (pulse wave data having a clear waveform) is used as output data. Further, in Embodiment 3, accurate pulse wave data is used as output data. The pulse wave data as the output data is data indicating a pulse wave that is an example of biological information. In Embodiment 4, an analysis condition (for example, a separation matrix) that contributes to the acquisition of accurate pulse wave data is used as output data.

Specifically, the data output unit 23 outputs output data generated on the basis of a plurality of pieces of analysis target data identified for each of the plurality of extraction conditions. The output data to be output is generated through randomly set processing. Processing for the data output unit 23 to generate output data and an example of the output data generated as a result of the processing will be described in detail in Embodiments 2 to 4 showing specific examples of the present embodiment.

The data output unit 23 outputs the generated output data to an external device as an output destination. When the input data includes, for example, biological information acquired from a living body, or when the output data includes biological information, the output destination may be, for example, a measuring device that measures the state of a living body on the basis of biological information (for example, pulse wave data). Examples of the state of a living body measured by the measuring device include heart rate, pulse rate, heartbeat interval, or stress level.

In addition, the output destination may be, for example, an analysis device that performs a predetermined analysis on the analysis target data, or a presentation device (for example, a display device or a speaker) that presents the analysis target data. The data analysis device 1 may be provided in the same device as the output destination. That is, the output destination includes the data analysis device 1.

In the present embodiment, the data extraction unit 21, the data identification unit 22, the data output unit 23, and the storage unit 3 are included in one device called the data analysis device 1, but the present disclosure is not limited thereto. The data extraction unit 21, the data identification unit 22, the data output unit 23, and the storage unit 3 may be separately provided in two or more and four or less devices. In this case, the data analysis device 1 is implemented by a plurality of devices.

The set of members provided in each device can be randomly selected. That is, the data extraction unit 21, the data identification unit 22, the data output unit 23, and the storage unit 3 may function as individual devices. Further, two or three members of the data extraction unit 21, the data identification unit 22, the data output unit 23, and the storage unit 3 may be implemented by one device. Further, the data analysis device 1 or each of the above devices may be implemented by a cloud.

Example of Input Data

FIGS. 2(a) to 2(c) are diagrams showing an example of input data. As described above, the input data is obtained by associating a secondary characteristic value with a primary characteristic value. The input data includes at least one set of the primary characteristic value and the secondary characteristic value. A collection of a plurality of secondary attributes corresponding to one primary attribute is a set of input data. In other words, the set of input data includes a plurality of pieces of input data in which attributes of the secondary characteristic value corresponding to the primary characteristic value are different from each other.

In the example of FIG. 2(a), the primary attribute is a "position", and three secondary attributes are a "signal Si1", a "signal Si2", and a "signal Si3". That is, in this example, the input data is composed of the following sets:

- a set of a primary characteristic value indicating the "position" and a secondary characteristic value indicating the "signal Si1";
- a set of a primary characteristic value indicating the "position" and a secondary characteristic value indicating the "signal Si2"; and
- a set of a primary characteristic value indicating the "position" and a secondary characteristic value indicating the "signal Si3".

The set of input data is a collection of these three pieces of input data.

The primary attribute and the secondary attribute may be any attribute. For example, the primary attribute may be a "time". When the primary attribute is a "time", the data analysis device 1 can perform processing on input data as time-series data.

The primary characteristic value and the secondary characteristic value are not limited to numerical values, and may be serial numbers, characters, labels, or symbols, for example. In the example of FIG. 2(b), the primary attribute is a "serial number (of the question)" and the secondary attribute is an "(individual) answer (to the question)". Further, as shown in FIG. 2(b), it is not always necessary that the secondary characteristic values are present for all the primary characteristic values (see "Answer B" of "No. 2").

Further, as shown in FIG. 2(c), the primary characteristic values may be different between the input data. In the example of FIG. 2(c), the primary characteristic value is a "time", and the secondary characteristic values are a "strength St1", a "strength St2", and a "strength St3". In this example, the initial values of the primary characteristic values of the three pieces of input data or the intervals between adjacent primary characteristic values (here, the time intervals) are different from each other.

Example of Processing by Data Extraction Unit

FIG. 3 is a diagram showing an example of processing of the data extraction unit 21. The data extraction unit 21 extracts, as the extracted data, a set of a primary characteristic value and a secondary characteristic value corresponding to each of the plurality of extraction conditions, for each of the plurality of pieces of input data that form the set of input data.

It is sufficient that the plurality of extraction conditions be different from each other. Further, the extraction condition may be a condition for continuously selecting a primary characteristic value from a plurality of primary characteristic values, or a condition for discretely selecting the primary characteristic values. Here, the plurality of extraction conditions are determined depending on whether or not the analysis target data identified from the extracted data by the data identification unit 22 satisfies the data condition necessary for the data output unit 23 to generate the output data.

Examples of setting a plurality of extraction conditions will be described in detail in Embodiments 2 to 4.

As shown in FIG. 3, the data extraction unit 21 applies an extraction condition C1 to each of input data D1 to D3 to generate extracted data DS1 (extracted data D11 to D13 corresponding to the input data D1 to D3, respectively). Specifically, in the example of FIG. 3, a set of primary characteristic values "1", "2" and "5" of a primary attribute "M" and secondary characteristic values corresponding to the primary characteristic values is extracted. Similarly, the data extraction unit 21 applies each of extraction conditions C2 to C4 to the input data D1 to D3 to generate extracted data DS2 to DS4 corresponding to the extraction conditions C2 to C4, respectively.

When a primary characteristic value selected by the extraction condition is not present in the input data, the data extraction unit 21 may leave the corresponding portion in the extracted data blank, assuming that the input data does not have the primary characteristic value corresponding to the extraction condition. Further, the data extraction unit 21 may also extract a set of a primary characteristic value close to the selected primary characteristic value and a secondary characteristic value corresponding to the primary characteristic value. In addition, by performing interpolation processing on the input data, the data extraction unit 21 may estimate a primary characteristic value and a secondary characteristic value corresponding to the extraction condition, and extract a set of the estimated primary characteristic value and secondary characteristic value.

Furthermore, when a secondary characteristic value corresponding to the primary characteristic value selected by the extraction condition is not present in the input data, the data extraction unit 21 may leave the corresponding portion in the extracted data blank, assuming that the secondary characteristic value is not present. In addition, by performing interpolation processing on the input data, the data extraction unit 21 may estimate a secondary characteristic value corresponding to the primary characteristic value corresponding to the extraction condition, and extract the estimated secondary characteristic value.

Example of Processing by Data Identification Unit

FIG. 4(a) is a diagram showing an example of processing of the data identification unit 22. When the plurality of pieces of extracted data extracted by the data extraction unit 21 are input, the data identification unit 22 identifies analysis target data as a result of performing predetermined analysis processing and predetermined selection processing.

For example, when independent component analysis is used as the predetermined analysis processing, as shown in FIG. 4(a), the data identification unit 22 applies a separation matrix ICA1 to the extracted data DS1 (extracted data D11, D12, D13, . . . ) corresponding to the extraction condition C1. As a result, the data identification unit 22 acquires analysis target candidate data IC1 (analysis target candidate data IC11, IC12, IC13, . . . ) as independent components. The data identification unit 22 performs predetermined selection processing to identify analysis target candidate data IC1$x$ to be included in analysis target data SD1 corresponding to the extraction condition C1 from the plurality of pieces of analysis target candidate data IC1.

For example, when the analysis target candidate data IC11 is identified as data to be included in the analysis target data SD1, the data identification unit 22 may assign a component number M1 to the analysis target candidate data IC11. The analysis target data SD1 may include data other than the identified analysis target candidate data IC11. The analysis target data SD1 includes, for example, the data described above and related to the analysis target candidate data IC11 in addition to the identified analysis target candidate data IC11. For example, the analysis target data SD1 includes the following elements:

the separation matrix ICA1 used to acquire the analysis target candidate data IC11;

the analysis target candidate data IC11, IC12, IC13, . . . acquired by applying the separation matrix ICA1 to the extracted data DS1; and the component number M1.

In addition, the analysis target data SD1 may include, for example, the S/N ratio of the analysis target candidate data IC11. Further, the analysis target data SD1 does not have to include all these data. It is sufficient that the analysis target data SD1 include data necessary for the data output unit 23 to generate output data.

Here, the predetermined selection processing is set according to the characteristics of the analysis target data or the like, and is processing of selecting the optimum analysis target candidate data included in the range of a value (target value) to be acquired as data to be included in analysis target data.

Similarly, the data identification unit 22 applies the separation matrices ICA2, ICA3, . . . to the extracted data DS2, DS3, . . . , corresponding to the extraction conditions C2, C3, . . . , respectively. Thereby, the data identification unit 22 generates, as an independent component, analysis target candidate data IC2 (analysis target candidate data IC21, IC22, IC23, . . . ) corresponding to the extraction condition C2, analysis target candidate data IC3 (analysis target candidate data IC31, IC32, IC33, . . . ) corresponding to the extraction condition C3, . . . .

Then, the data identification unit 22 performs the same selection processing (selection processing under the same conditions) as in the case of the extraction condition C1 to identify analysis target data SD2, SD3, . . . , corresponding to the extraction conditions C2, C3, . . . , respectively. The analysis target data SD2, SD3, . . . include the data similar to the analysis target data SD1.

In the case of the independent component analysis, when the extracted data extracted from n pieces of input data is (D11, D12, . . . , D1n), the independent components (IC11, IC12, . . . , IC1n) are separated by the separation matrix ICA1 (n rows×n columns) as shown below:

$$(IC11, IC12, \ldots, IC1n) = (D11, D12, \ldots, D1n) \times ICA1$$

This expression means a linear transformation by the separation matrix ICA1 from the vectors (D11, D12, . . . , D1n) as the extracted data to the vectors (IC11, IC12, . . . , IC1n) as the independent component. In the independent component analysis, the separation matrix ICA1 is determined so that the linearly transformed independent components (IC11, IC12, . . . , IC1n) are independent of each other. The separation matrix ICA1 is determined using a predetermined numerical calculation algorithm (for example, an infomax method or a fastICA method).

Further, in the case of the principal component analysis, when the extracted data extracted from n pieces of input data is (D11, D12, . . . , D1n), principal components (PC11, PC12, . . . , PC1n) are separated by an orthogonal matrix PCA1 (n rows×n columns) as shown below:

$$(PC11, PC12, \ldots, PC1n) = (D11, D12, \ldots, D1n) \times PCA1$$

This expression means a linear transformation by the orthogonal matrix PCA1 from the vectors (D11, D12, . . . , D1n) as the extracted data to the vectors (PC11, PC12, . . . , PC1n) as the principal component. In the principal component analysis, the orthogonal matrix PCA1 is determined so that the variance increases in the order of PC11, PC12, . . . , PC1n in the linearly transformed principal components (PC11, PC12, . . . , PC1n).

Since the extraction conditions are different from each other, the extracted data before transformation by the independent component analysis or the principal component analysis differs, such as (D11, D12, . . . , D1n), (D21, D22, . . . , D2n), . . . , for each extraction condition. Therefore, the separation matrices ICA1, ICA2, . . . or the orthogonal matrices PCA1, PCA2, . . . calculated on the basis of the extracted data of each extraction condition also differ for each extraction condition.

In this specification, the analysis target candidate data is mainly described as an independent component. Therefore, IC1, IC2, . . . , are used as the reference signs of the analysis target candidate data. However, when the principal component analysis is performed as the predetermined analysis processing, the analysis target candidate data is the principal components mentioned above, and therefore PC11, PC12, . . . , PC1n may be used as the reference signs of the analysis target candidate data.

FIG. 4(b) is a diagram showing an example of the analysis target data stored in the storage unit 3. In the example of FIG. 4(b), the analysis target data is stored in association with the extraction condition. However, only the analysis target data may be stored. The data output unit 23 performs predetermined processing on the analysis target data stored in the storage unit 3 to generate output data to be output (for example, a signal itself less affected by a variation factor).

Here, the variation factor is a factor (for example, noise or an abnormal value included in the input data) that changes the result of the analysis processing by affecting the analysis processing on the input data. Further, the predetermined processing refers to processing for selecting, from a plurality of pieces of analysis target candidate data, analysis target data which does not include a variation factor or influence of the variation factor on which is suppressed.

<Processing in Data Analysis Device>

Figure 5:
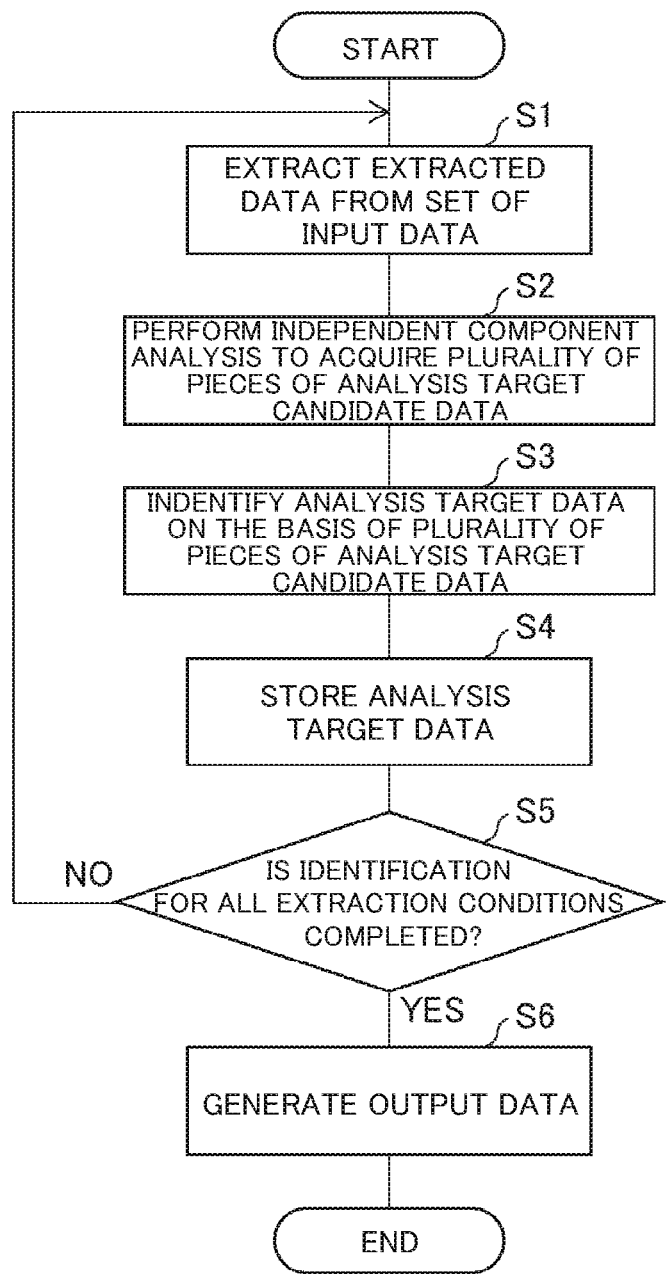
FIG. 5 is a diagram showing an example of processing in the data analysis device.

FIG. 5 is a flowchart showing an example of processing in the data analysis device 1. As shown in FIG. 5, the data extraction unit 21 extracts extracted data according to any extraction condition, from a set of input data (S1). Specifically, the data extraction unit 21 generates extracted data D11, D12, . . . according to the extraction condition C1 for each of input data D1, D2, included in a set IN of input data.

Next, the data identification unit 22 performs predetermined analysis processing (for example, an independent component analysis) on the extracted data D11, D12, . . . and identifies analysis target data SD1 on the basis of the result of the analysis processing. For example, the data identification unit 22 performs processing using a separation matrix ICA1 set according to the extraction condition C1 to acquire a plurality of pieces of analysis target candidate data IC11, IC12, . . . (S2). The data identification unit 22 identifies the analysis target data SD1 on the basis of the plurality of pieces of acquired analysis target candidate data IC11, IC12, . . . (S3). The data identification unit 22 stores the identified analysis target data SD1 in the storage unit 3 (S4).

When the data identification unit 22 completes the identification of the analysis target data corresponding to the extraction condition, the data extraction unit 21 determines whether or not the analysis target data is identified for all the extraction conditions (S5). When the analysis target data is not identified for all the extraction conditions (NO in S5), the processing of S1 to S4 is performed until the analysis target data is identified for all the extraction conditions.

In the above example, after the analysis target data SD1 corresponding to the extraction condition C1 is identified, the data extraction unit 21 determines that analysis target data SD2, . . . corresponding to other extraction conditions C2, . . . are not identified. In this case, the data extraction unit 21 performs the processing of S1 to S4 on the same input data (input data D1, D2, . . . ) as the input data to which the extraction condition C1 is applied in order to identify the analysis target data SD2, SD3, . . . in the order of the extraction conditions C2, C3, . . . .

When the data extraction unit 21 determines that the analysis target data SD1, SD2, . . . are identified for all the extraction conditions C1, C2, . . . , respectively (YES in S5), the data output unit 23 generates output data on the basis of the analysis target data SD1, SD2, . . . (S6).

The analysis target data identified in S3 may include the analysis target candidate data selected from the plurality of pieces of analysis target candidate data for each extraction condition, as described above. Further, the analysis target data may include a predetermined characteristic (for example, a S/N ratio) of the selected analysis target candidate data, or may include an analysis condition. Further, in S4, the data identification unit 22 may store the identified analysis target data in the storage unit 3 in association with the extraction condition.

Effect

The data analysis device 1 extracts, as extracted data, a set of a primary characteristic value and a secondary characteristic value from a set of input data according to each of a plurality of extraction conditions which are different from each other, and performs predetermined analysis processing on each of the extracted data. Then, analysis target data is identified on the basis of the result of the analysis processing.

In general, the variation factor mentioned above may be included in the input data. When the input data includes a variation factor, a component acquired by the predetermined analysis processing is affected by the variation factor. Therefore, it is difficult to acquire accurate information (data with high reliability as data to be analyzed, for example, pulse wave data having a clear waveform) from the component. That is, in order to acquire accurate information, it is ideal to extract information from input data that does not include a variation factor.

Here, when only input data is given and it is attempted to extract accurate information from the input data, the extracted information is affected by the variation factor. On the other hand, when extracting extracted data from input data and extracting accurate information from the extracted data, it is sufficient that, as an extraction condition for extracting the extracted data, an ideal extraction condition be set which is capable of extracting the information while maximally suppressing the influence of the variation factor. However, it is not possible for the data analysis device to determine what type of a variation factor is included in input data only from the input data, and therefore it is not possible to preset ideal extraction conditions. Therefore, the data analysis device 1 prepares a plurality of extraction conditions different from each other, and identifies analysis target data corresponding to each of the extracted data extracted for each extraction condition. Then, by comparing these analysis target data, or by performing processing such as weighting using the analysis target data, it is possible to acquire analysis target data that is the same as or similar to analysis target data acquired when extraction is performed under ideal extraction conditions.

That is, by preparing a plurality of extraction conditions (extraction methods) different from each other, it is possible to increase the possibility of extracting the extracted data so as not to include the variation factor or to suppress the influence of the variation factor. That is, it is possible to acquire information that is the same as or similar to the information acquired under the ideal extraction conditions.

Therefore, according to the data analysis device 1, even when a signal to be analyzed includes a variation factor, it is possible to increase the possibility of extracting the signal less affected by the variation factor.

Embodiment 2

Another embodiment of the present disclosure will be described below. For convenience of description, members having the same functions as those described in the above embodiment are denoted by the same reference signs, and the description thereof will not be repeated. The same applies to embodiments subsequent to Embodiment 2.

Figure 6:
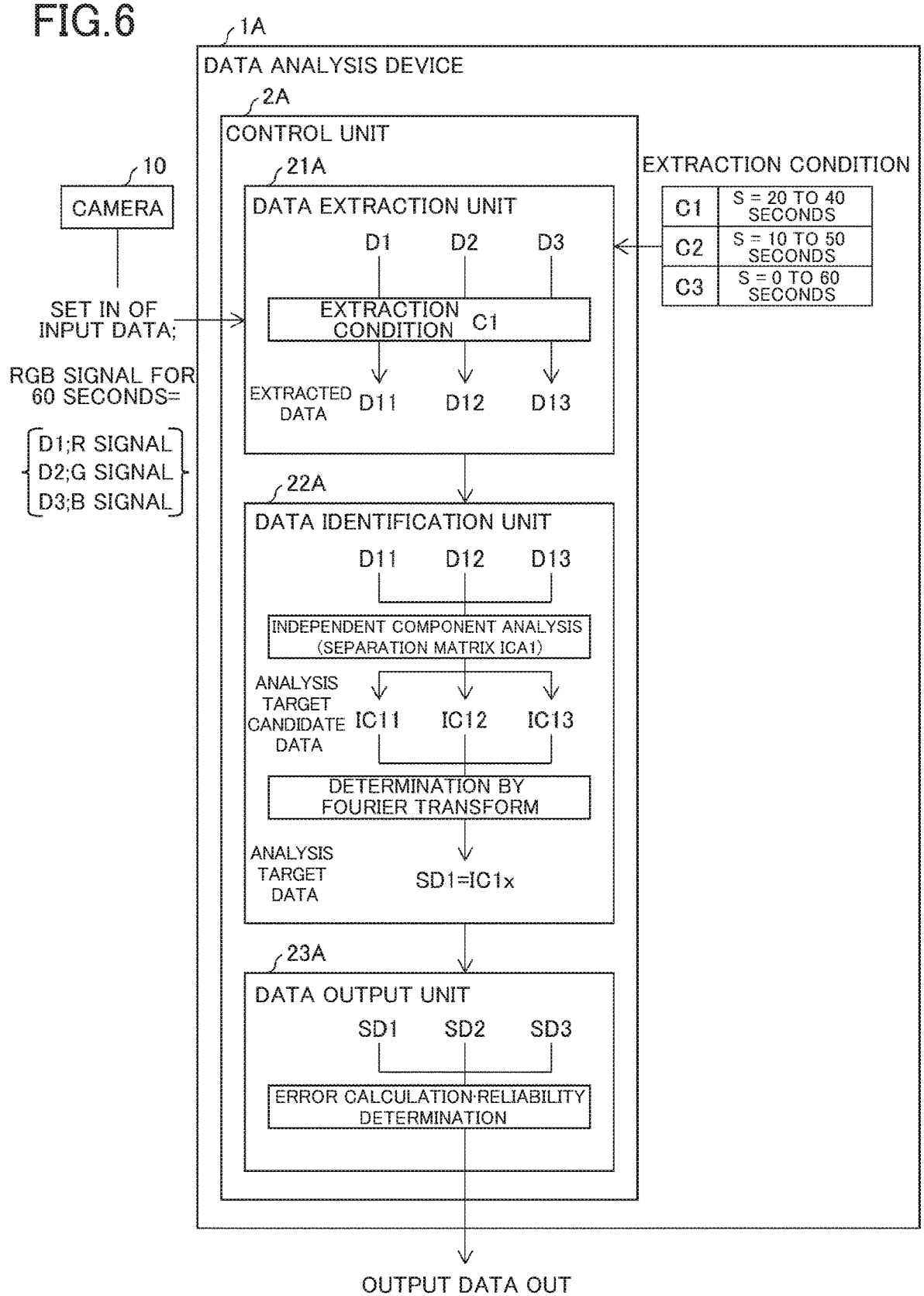
FIG. 6 is a block diagram showing an example of a data analysis device according to Embodiment 2.

FIG. 6 is a block diagram showing an example of a data analysis device 1A. The data analysis device 1A is one of the examples of the data analysis device 1. The data analysis device 1A determines the reliability of pulse wave data indicating a pulse wave as biological information acquired from color data (RGB signals) indicating the color of the skin of a living body. As shown in FIG. 6, the data analysis device 1A includes a control unit 2A and the storage unit 3 (not shown). The control unit 2A includes a data extraction unit 21A, a data identification unit 22A, and a data output unit 23A.

The data extraction unit 21A, the data identification unit 22A, and the data output unit 23A have the functions similar to the data extraction unit 21, the data identification unit 22, and the data output unit 23 of the control unit 2 of Embodiment 1, but differ in the following points.

Input data that is an extraction source of the data extraction unit 21A is moving image data acquired by a camera 10 that images a target object that is an acquisition target of analysis target candidate data. Further, in the present embodiment, the imaging target (target object) of the camera 10 is a predetermined part of the living body. That is, the input data includes biological information acquired from the living body. Specifically, the image represented by the moving image data acquired by the camera 10 includes an image of the living body.

In the data analysis device 1A, the data extraction unit 21A extracts the RGB signal by analyzing the moving image data (image of the living body). The RGB signal is time-series data whose primary attribute is a "time". That is, the input data that is an extraction source of the data extraction unit 21A is R time-series data (R signal), G time-series data (G signal), and B time-series data (B signal). In the present embodiment, the R signal, the G signal, and the B signal as input data are referred to as D1, D2, and D3, respectively.

Further, the RGB signal includes pulse wave data indicating a pulse wave as biological information. In the present embodiment, the data identification unit 22A performs the independent component analysis on the RGB signal acquired from the living body to acquire the pulse wave data as the analysis target data.

Further, in the present embodiment, the R signal D1, the G signal D2, and the B signal D3 are continuous signals for 60 seconds. The range of the "time" in the R signal D1, the G signal D2, and the B signal D3 is set as the extraction condition. The extraction conditions are set as follows, for example, C1: a range including the central 20 seconds of the R signal D1, the G signal D2, and the B signal D3 (that is, a range of 20 seconds or more and 40 seconds or less after the start of imaging), C2: a range including the central 40 seconds of the R signal D1, the G signal D2, and the B signal D3 (that is, a range of 10 seconds or more and 50 seconds or less after the start of imaging), and C3: a range including the central 60 seconds of the R signal D1, the G signal D2, and the B signal D3 (that is, a range (entire range) of 0 seconds or more and 60 seconds or less after the start of imaging).

The data extraction unit 21A extracts extracted data D11, D12, and D13 from the R signal D1, the G signal D2, and the B signal D3 forming a set IN of input data, respectively, according to the extraction condition C1. The data identification unit 22A applies a separation matrix ICA1 to the extracted data D11, D12, and D13 to acquire analysis target candidate data IC11, IC12, and IC13.

The data identification unit 22A performs predetermined selection processing to select analysis target candidate data IC1x estimated to be the pulse wave data from the analysis target candidate data IC11, IC12, and IC13. The data identification unit 22A executes, for example, a Fourier transform on each of the analysis target candidate data IC11, IC12, and IC13. Then, the data identification unit 22A selects the analysis target candidate data IC1x having the highest signal strength in a predetermined frequency range from the analysis target candidate data IC11, IC12, and IC13 after the Fourier transform, and identifies it as analysis target data SD1. In the present embodiment, the predetermined frequency range is set to, for example, 0.75 Hz or more and 4 Hz or less. Through this processing, the analysis target candidate data IC1x estimated to be pulse wave data can be selected.

Similar to the case of the extraction condition C1, the data extraction unit 21A extracts extracted data D21 to D23 according to the extraction condition C2. The data identification unit 22A applies a separation matrix ICA2 to the extracted data D21 to D23 to acquire analysis target candidate data IC21, IC22, and IC23. The data identification unit 22A executes the Fourier transform on the analysis target candidate data IC21, IC22, and IC23. Then, analysis target candidate data IC2x having the highest signal strength in a predetermined frequency range is selected from the analysis target candidate data IC21, IC22, and IC23 after the Fourier transform, and analysis target candidate data IC2x is identified as analysis target data SD2. Further, similarly, the data identification unit 22A applies a separation matrix ICA3 to extracted data D31 to D33 extracted according to the extraction condition C3 to acquire analysis target candidate data IC31, IC32, and IC33. Then, analysis target candidate data IC3x selected by the above method is identified as analysis target data SD3.

In this way, the data identification unit 22A identifies, as the analysis target data SD1, one (analysis target candidate data IC1x) of the plurality of pieces of analysis target candidate data IC11, IC12, and IC13 (analysis results) obtained by performing the independent component analysis. The data identification unit 22A similarly identifies the analysis target data SD2 and SD3.

In the present embodiment, the data output unit 23A performs the processing for determining the reliability of the analysis target data SD1 to SD3 to generate data indicating the determination result of the reliability as output data OUT.

Specifically, the data output unit 23A outputs, as output data, the result of comparison between the analysis target data SD1 to SD3. More specifically, the data output unit 23A compares the identified analysis target data SD1 to SD3 (analysis target candidate data IC1x, IC2x, and IC3x) with each other in the range of the central 20 seconds, which is a range overlapping in all the extraction conditions. The data output unit 23A selects any two from the identified analysis target data SD1 to SD3, and calculates a difference (error) in amplitude between the selected two data at each time in the range of the central 20 seconds. In this example, the error between the analysis target data SD1 and SD2, the error between the analysis target data SD1 and SD3, and the error between the analysis target data SD2 and SD3 are calculated.

When there is an error whose maximum value is equal to or greater than a predetermined value (for example, 100) among the calculated errors, the data output unit 23A determines that the reliability as pulse wave data of the analysis target data SD1 to SD3 is low. That is, it is determined that the RGB signal as the input data includes a variation factor (for example, noise). On the other hand, when the maximum value of the calculated errors is less than the predetermined value, the data output unit 23A determines that the reliability as pulse wave data of the analysis target data SD1 to SD3 is high. That is, it is determined that the RGB signal as the input data does not include a variation factor (for example, noise), or is a variation factor that can be ignored even if it is included. The data output unit 23A outputs this determination result as the output data OUT.

In this way, the data analysis device 1A compares a plurality of pieces of analysis target data corresponding to one primary attribute to generate output data. Specifically, the data analysis device 1A compares a plurality of pieces of analysis target data in the range of one primary characteristic value (here, one time range) to calculate an error of the waveform indicated by the analysis target data and determine the reliability of the analysis target data on the basis of the error. Therefore, the primary characteristic values in the one range to be compared by the data identification unit 22A are set in all the extraction conditions. In other words, each of all the extraction conditions is set to include a plurality of primary characteristic values included in the specific range and a plurality of secondary characteristic values corresponding to the plurality of primary characteristic values. In the present embodiment, the range of the central 20 seconds to be compared by the data identification unit 22A is set for all extraction conditions. It should be noted that the primary characteristic values in the one range to be compared under all extraction conditions are not limited to the above range and can be randomly set. In addition, the number of extraction conditions can be randomly set.

In the data analysis device 1A, the analysis target candidate data (that is, the signal wave as the time-series data) is used as the analysis target data. When the data identification unit 22A separates the extracted data into analysis target candidate data having a desired waveform (for example, a clear waveform as pulse wave data), a certain number of primary characteristic values are required. In other words, when the number of sets of the primary characteristic value and the secondary characteristic value in the extracted data is extremely small, the extracted data may not be separated into analysis target candidate data having a desired waveform. For example, when it is desired to acquire a waveform of the pulse wave data of about 1 Hz, the waveform cannot be acquired from the extracted data including only about one set of a primary characteristic value and a secondary characteristic value per second.

That is, a plurality of extraction conditions (the number of sets of a primary characteristic value and a secondary characteristic value to be extracted) are determined depending on the clearness degree of the waveform of the analysis target candidate data to be acquired. For example, the extraction condition is set so that the extracted data having a continuous set of the primary characteristic value and the secondary characteristic value to the extent that the analysis target candidate data having a clear waveform as the pulse wave data can be acquired can be extracted.

The setting of the extraction condition for the set of the primary characteristic value and the secondary characteristic value is the same for a data analysis device 1B of Embodiment 3 and a data analysis device 1C of Embodiment 4.

Further, a predetermined frequency range used when selecting the analysis target candidate data to be included in the analysis target data and a predetermined value to be compared with the maximum value of the error are not limited to the values mentioned above. It is sufficient that the predetermined frequency range be set to a range in which the analysis target candidate data estimated to be the pulse wave data can be selected. Further, it is sufficient that the predetermined value be set to a value with which it can be determined that the variation factor is included in the input data that is the extraction source. The predetermined frequency range and the predetermined value are set through, for example, experiments.

Further, the data identification unit 22A includes, in the analysis target data, the analysis target candidate data acquired as a result of performing the independent component analysis on the extracted data, but the present disclosure is not limited thereto, and the separation matrix may be included. In this case, the data output unit 23A may output, as output data, a result of comparison between a plurality of separation matrices as the analysis target data. For example, the data output unit 23A may calculate a difference between any two separation matrices for the plurality of separation matrices, and determine whether or not the maximum value of the difference is less than the determination criterion, thereby determining the reliability of the selected analysis target candidate data and outputting the determination result. The data output unit 23A may digitize the reliability and output the digitized reliability as output data.

EXAMPLE

Figure 7:
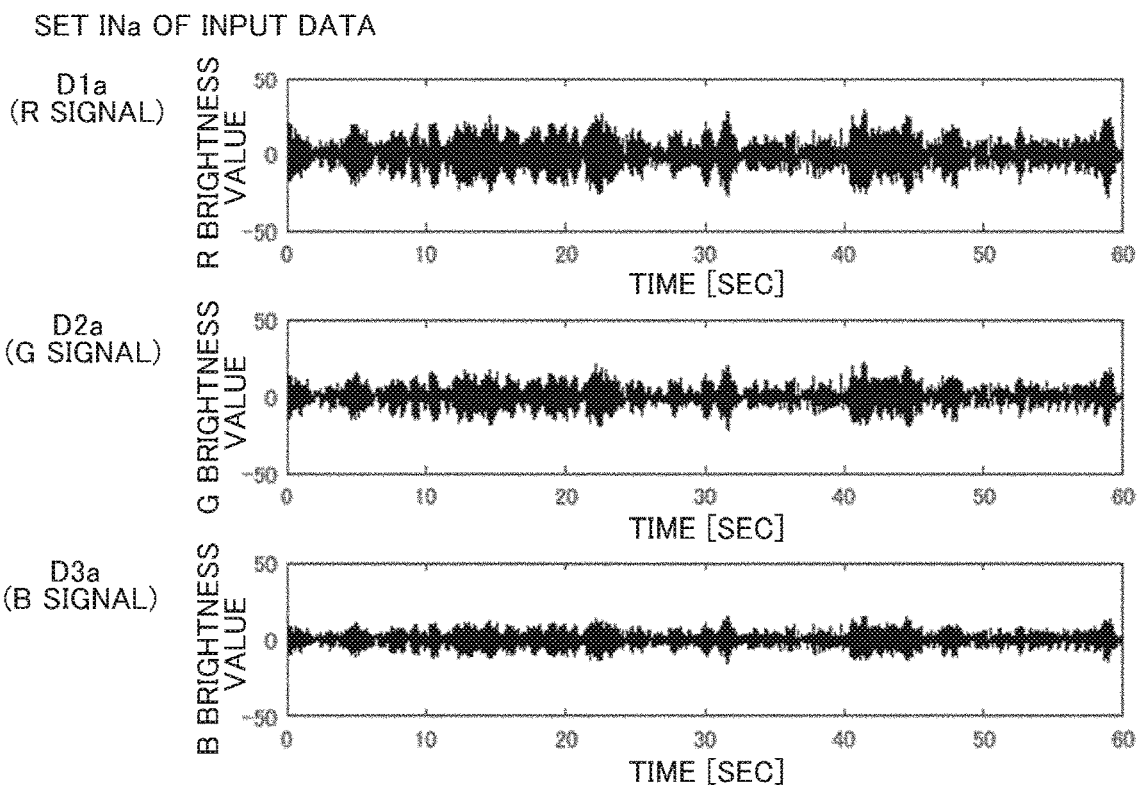
FIG. 7 is a diagram showing an example of a set of input data.
Figure 8:
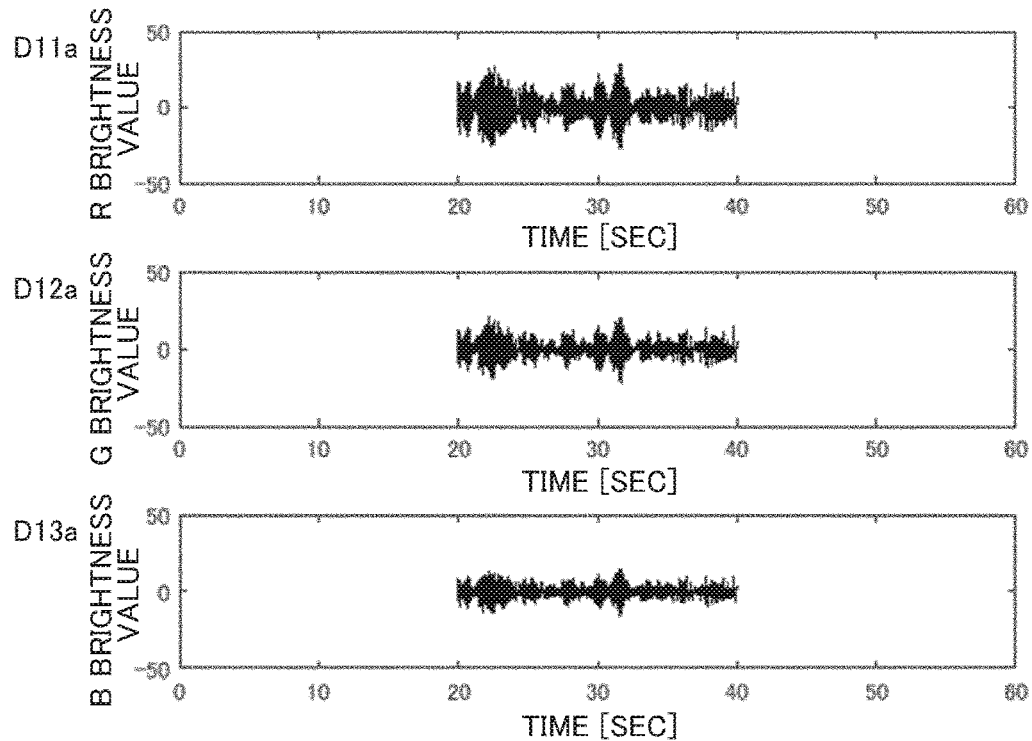
FIG. 8 is a diagram showing an example of extracted data extracted according to an extraction condition, from the set of input data of FIG. 7.

FIG. 7 is a diagram showing an example of a set INa of input data. FIG. 8 is a diagram showing an example of extracted data DS1a extracted according to the extraction condition C1, from the set INa of input data of FIG. 7. FIG. 9 is a diagram showing an example of analysis target candidate data IC1a acquired by applying the separation matrix ICA1 to the extracted data DS1a of FIG. 8. FIG. 10 is a diagram showing an example of analysis target data SDa corresponding to the extraction conditions C1 to C3.

When the set INa of input data is composed of an R signal D1a, a G signal D2a, and a B signal D3a as shown in FIG. 7, the data extraction unit 21A extracts the range of the central 20 seconds indicated by the extraction condition C1 from each of the R signal D1a, the G signal D2a, and the B signal D3a. As a result, the data extraction unit 21A extracts extracted data D11a corresponding to the R signal D1a, extracted data D12a corresponding to the G signal D2a, and extracted data D13a corresponding to the B signal D3a, as shown in FIG. 8.

The data identification unit 22A applies a separation matrix ICA1 to the extracted data D11a, D12a, and D13a of FIG. 8 to acquire analysis target candidate data IC11a, IC12a, and IC13a of FIG. 9. The data identification unit 22A executes the Fourier transform on the analysis target candidate data IC11a, IC12a, and IC13a. Then, as shown in FIG. 10, from the analysis target candidate data IC11a, IC12a, and IC13a after the Fourier transform, the analysis target candidate data IC12a having the highest signal strength in a frequency range of 0.75 Hz or more and 4 Hz or less is identified as analysis target data SD1a.

Further, the data extraction unit 21A and the data identification unit 22A perform processing based on the extraction condition C2 on the set INa of input data to identify analysis target data SD2a shown in FIG. 10. Similarly, the data extraction unit 21A and the data identification unit 22A perform processing based on the extraction condition C3 on the set INa of input data to identify analysis target data SD3a shown in FIG. 10.

When the data output unit 23A calculates the error mentioned above for the analysis target data SD1a to SD3a shown in FIG. 10, the maximum value thereof is 69.9. Since this value is less than the predetermined value of 100, the data output unit 23A determines that the reliability of the pulse wave data (analysis target data SDa) obtained from the set INa of input data is high, and outputs the output data OUT indicating "reliable".

Figure 11:
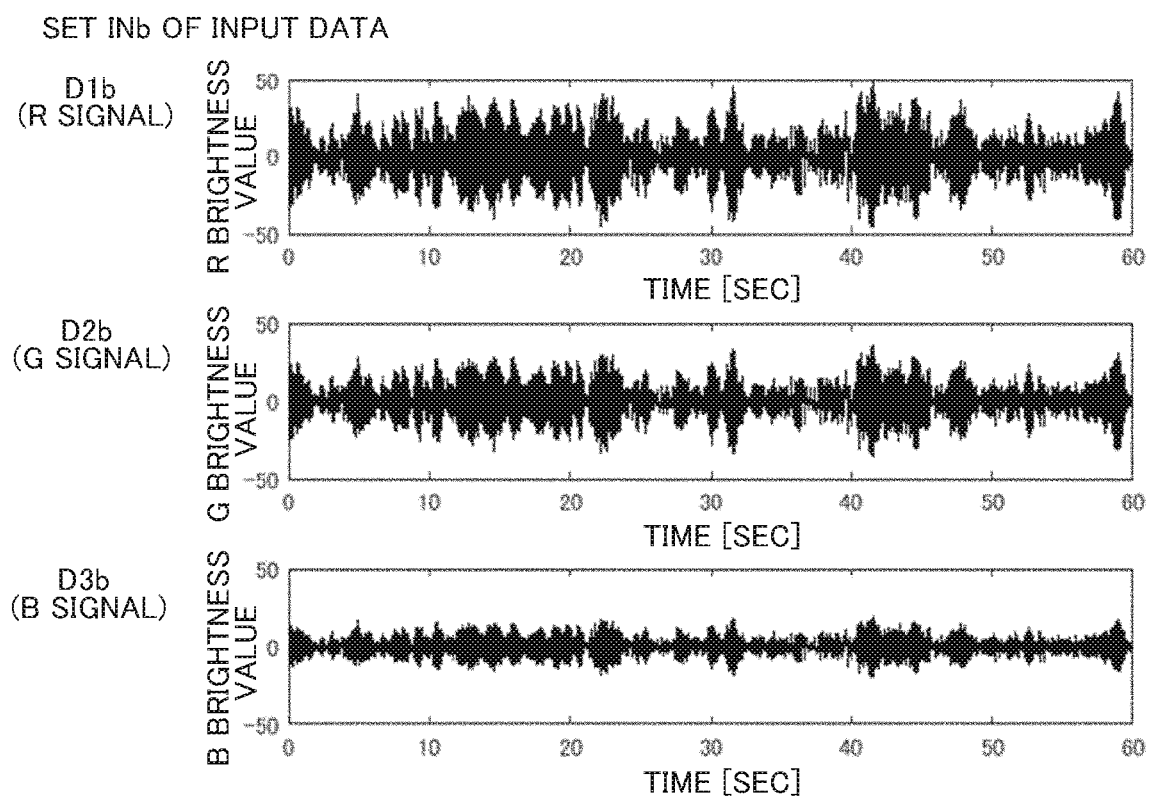
FIG. 11 is a diagram showing an example of a set of input data different from that of FIG. 7.

Next, the result of verification of the reliability of the pulse wave data obtained from a set INb of input data different from the set INa of input data will be shown. FIG. 11 is a diagram showing an example of the set INb of input data. FIG. 12 is a diagram showing an example of analysis target data SDb corresponding to the extraction conditions C1 to C3.

As shown in FIG. 11, the set INb of input data is composed of an R signal D1b, a G signal D2b, and a B signal D3b. In this case, the data extraction unit 21A and the data identification unit 22A perform processing based on each of the extraction conditions C1 to C3 on the set INb of input data to identify the analysis target data SDb shown in FIG. 12. Specifically, the data identification unit 22A identifies analysis target data SD1b corresponding to the extraction condition C1, analysis target data SD2b corresponding to the extraction condition C2, and analysis target data SD3b corresponding to the extraction condition C3.

When the data output unit 23A calculates the error mentioned above for the analysis target data SD1b to SD3b shown in FIG. 12, the maximum value thereof is 301.3. Since this value exceeds the predetermined value of 100, the data output unit 23A determines that the reliability of the pulse wave data (analysis target data SDb) obtained from the set INb of input data is low, and outputs the output data OUT indicating "unreliable".

Effect

The data analysis device 1A can increase the possibility of extracting pulse wave data less affected by a variation factor even when the RGB signal acquired from the living body includes the variation factor.

The data analysis device 1A also calculates the error of the analysis target data as the pulse wave data acquired for each extraction condition, and outputs the reliability of the pulse wave data on the basis of the calculation result. Therefore, the data analysis device 1A can issue a notification of the reliability of the acquired pulse wave data. By this notification, for example, highly reliable pulse wave data can be selectively used in the measuring device, and thus various types of information indicating the state of the living body such as the pulse rate can be accurately measured.

Further, when the input data is moving image data, the input data can be acquired by a simple method of capturing an image with the camera 10. In addition, by imaging a predetermined part of a living body with the camera 10, moving image data including the image of the living body can be acquired. In this case, an RGB signal capable of extracting biological information (for example, pulse wave data) can be acquired from the image of the living body.

Embodiment 3

Figure 13:
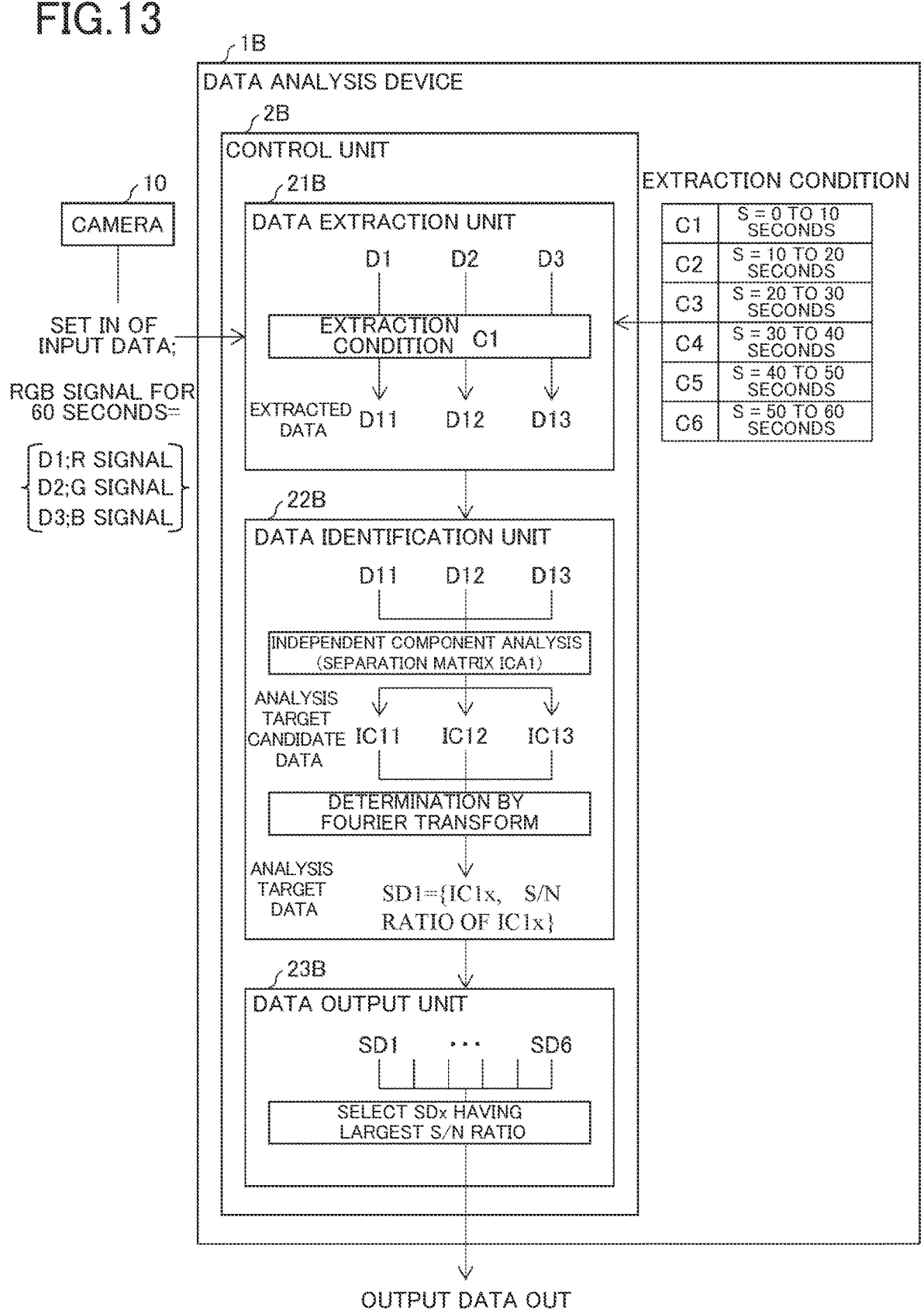
FIG. 13 is a block diagram showing an example of a data analysis device according to Embodiment 3.

FIG. 13 is a block diagram showing an example of a data analysis device 1B. The data analysis device 1B is one of the examples of the data analysis device 1. The data analysis device 1B identifies the range of pulse wave data acquired from an RGB signal, which is estimated to have high reliability. As shown in FIG. 13, the data analysis device 1B includes a control unit 2B and the storage unit 3 (not shown). The control unit 2B includes a data extraction unit 21B, a data identification unit 22B, and a data output unit 23B.

The data extraction unit 21B, the data identification unit 22B, and the data output unit 23B have the functions similar to the data extraction unit 21A, the data identification unit 22A, and the data output unit 23A of the control unit 2A of Embodiment 2, but differ in the following points.

The data extraction unit 21B extracts extracted data D11 to D13 from a set IN of input data (R signal D1, G signal D2, and B signal D3) according to the extraction condition different from that of Embodiment 2. As for the extraction condition of the present embodiment, in the R signal D1, the G signal D2, and the B signal D3, different ranges of the "time" are set for each extraction condition. The extraction conditions are set as follows, for example, C1: a range of 0 seconds or more and less than 10 seconds of the R signal D1, the G signal D2, and the B signal D3,
C2: a range of 10 seconds or more and less than 20 seconds of the R signal D1, the G signal D2, and the B signal D3,
C3: a range of 20 seconds or more and less than 30 seconds of the R signal D1, the G signal D2, and the B signal D3,
C4: a range of 30 seconds or more and less than 40 seconds of the R signal D1, the G signal D2, and the B signal D3,
C5: a range of 40 seconds or more and less than 50 seconds of the R signal D1, the G signal D2, and the B signal D3, and
C6: a range of 50 seconds or more and 60 seconds or less of the R signal D1, the G signal D2, and the B signal D3.

As in Embodiment 2, the data identification unit 22B performs independent component analysis on the extracted data D11, D12, and D13 extracted by the data extraction unit 21B according to the extraction condition C1 to acquire analysis target candidate data IC11, IC12, and IC13. The data identification unit 22B identifies, as analysis target candidate data to be included in analysis target data SD1, analysis target candidate data IC1$x$ having the highest signal strength in a predetermined frequency range from the acquired analysis target candidate data IC11, IC12, and IC13 after the Fourier transform. The predetermined frequency range is a range of, for example, 0.75 Hz or more and 4 Hz or less, as in Embodiment 2.

In addition, the data identification unit 22B calculates a S/N ratio (value related to the quality of the analysis result) of the analysis target candidate data IC1$x$ having the highest signal strength in the predetermined frequency range, and includes the S/N ratio in the analysis target data SD1. That is, in the present embodiment, the data identification unit 22B generates the analysis target data SD1 including the analysis target candidate data IC1$x$ having the highest signal strength in the predetermined frequency range and the S/N ratio of the analysis target candidate data IC1$x$.

The data extraction unit 21B and the data identification unit 22B also perform the same processing as the processing on the extraction condition C1 for the extraction conditions C2 to C6 to generate analysis target data SD2 to SD6 respectively corresponding to the extraction conditions C2 to C6. Similar to the analysis target data SD1, the analysis target data SD2 to SD6 include analysis target candidate data IC2$x$ to IC6$x$ having the highest signal strength in a predetermined frequency range and S/N ratios (values related to the quality of the analysis result) of the analysis target candidate data IC2$x$ to IC6$x$, respectively.

The data output unit 23B performs processing for extracting the analysis target candidate data estimated to have high reliability as the pulse wave data from the analysis target candidate data included in each of the plurality of pieces of analysis target data. Then, the data output unit 23B generates analysis target candidate data extracted as the result of the processing as output data OUT.

Specifically, the data output unit 23B outputs, as output data, the result of comparison between the analysis target data SD1 to SD6. More specifically, the data output unit 23B compares the S/N ratios of the analysis target data SD1 to SD6 to select the analysis target data having the largest S/N ratio among the analysis target data SD1 to SD6. That is, the data output unit 23B identifies the analysis target candidate data IC1$x$ to IC6$x$ estimated to have the highest reliability as the pulse wave data under each of the extraction conditions C1 to C6, and selects the analysis target candidate data having the least influence of the variation factor from among them. Thereby, when the set IN of input data is divided at a predetermined time interval (every 10 seconds in this example), the signal wave having the highest reliability as the pulse wave data can be selected from the signal waves (analysis target candidate data IC1$x$ to IC6$x$) acquired corresponding to each part of the set IN of input data.

In this way, the data analysis device 1B compares the S/N ratios of the analysis target candidate data separated for each extraction condition to identify the optimum analysis target candidate data. Therefore, the S/N ratios to be compared are calculated from the analysis target candidate data acquired under the same condition. That is, each extraction condition is set to have the same condition. Therefore, in the present embodiment, in each extraction condition, the number of a plurality of primary characteristic values to be extracted and an extraction interval of the plurality of primary characteristic values are the same (in the above example, an interval of 10 seconds).

The data analysis device 1C of Embodiment 4 also uses the S/N ratio of the analysis target candidate data acquired under each extraction condition. Therefore, also in Embodiment 4, each extraction condition is set to have the same condition as in the present embodiment (also in Embodiment 4, in each extraction condition, the number and the interval of primary characteristic values to be extracted are the same).

Further, as described in Embodiment 2, also in the present embodiment, each extraction condition is set so that the extracted data having a continuous set of the primary characteristic value and the secondary characteristic value can be extracted. Therefore, the S/N ratio of the analysis target candidate data acquired from the extracted data can be calculated.

Effect

The data analysis device 1B can extract pulse wave data less affected by a variation factor. Further, the data analysis device 1B can provide an output destination with the range of the pulse wave data estimated to have the highest reliability. When the output destination is the measuring device, the measuring device can measure the state of the living body using the range, and thus the accurate measurement can be performed.

Embodiment 4

Figure 14:
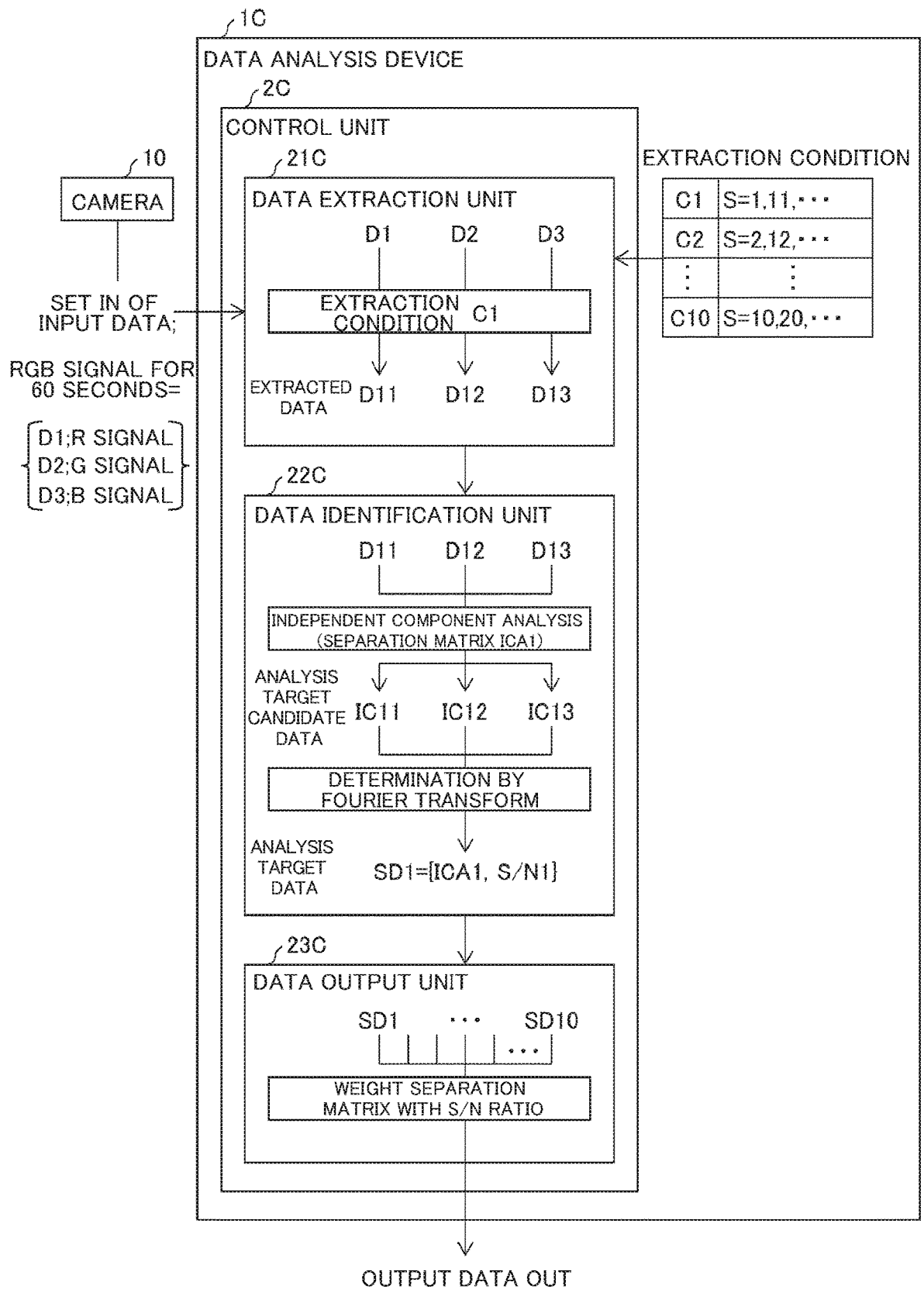
FIG. 14 is a block diagram showing an example of a data analysis device according to Embodiment 4.

FIG. 14 is a block diagram showing an example of a data analysis device 1C. The data analysis device 1C is one of the examples of the data analysis device 1. The data analysis device 1C performs processing for acquiring pulse wave data estimated to have high reliability from an RGB signal that forms moving image data imaged by the camera 10 for 60 seconds. As shown in FIG. 14, the data analysis device 1C includes a control unit 2C and the storage unit 3 (not shown). The control unit 2C includes a data extraction unit 21C, a data identification unit 22C, and a data output unit 23C.

The data extraction unit 21C, the data identification unit 22C, and the data output unit 23C have the functions similar to the data extraction unit 21A, the data identification unit 22A, and the data output unit 23A of the control unit 2A of Embodiment 2, but differ in the following points.

The data extraction unit 21C extracts extracted data Dx1 to Dx3 from a set IN of input data (R signal D1, G signal D2, and B signal D3) according to an extraction condition Cx different from that of Embodiment 2. The extraction condition of the present embodiment is set so that a set of a primary characteristic value and a secondary characteristic value can be extracted for every several frames (for example, every 10 frames) of moving image data forming the R signal D1, the G signal D2, and the B signal D3. When the moving image data for 60 seconds is composed of 100 frames, the extraction conditions are set as follows, for example, C1: R signal D1, G signal D2, and B signal D3 of 1 frame, 11 frames, 21 frames, . . . , 81 frames, and 91 frames, C2: R signal D1, G signal D2, and B signal D3 of 2 frames, 12 frames, 22 frames, . . . , 82 frames, and 92 frames,

. . .

C9: R signal D1, G signal D2, and B signal D3 of 9 frames, 19 frames, 29 frames, . . . , 89 frames, and 99 frames, and C10: R signal D1, G signal D2, and B signal D3 of 10 frames, 20 frames, 30 frames, . . . , 90 frames, and 100 frames.

As in Embodiment 3, the data identification unit 22C applies a separation matrix ICA1 to extracted data D11, D12, and D13 extracted according to the extraction condition C1 to acquire analysis target candidate data IC11, IC12, and IC13. The data identification unit 22C selects analysis target candidate data IC1x having the highest signal strength in a predetermined frequency range from the analysis target candidate data IC11, IC12, and IC13 after the Fourier transform. The predetermined frequency range is a range of, for example, 0.75 Hz or more and 4 Hz or less. Further, the data identification unit 22C calculates a S/N ratio of the analysis target candidate data IC1x having the highest signal strength in the predetermined frequency range, as in Embodiment 3. Then, the data identification unit 22C generates analysis target data SD1 including the separation matrix ICA1 and the S/N ratio of the analysis target candidate data IC1x having the highest signal strength in the predetermined frequency range.

The data extraction unit 21C and the data identification unit 22C also perform the same processing as the processing on the extraction condition C1 for the extraction conditions C2 to C10 to generate analysis target data SD2 to SD10 respectively corresponding to the extraction conditions C2 to C10. Similar to the analysis target data SD1, the analysis target data SD2 to SD10 include separation matrices ICA2 to ICA10 and S/N ratios of analysis target candidate data IC2x to IC10x having the highest signal strength in a predetermined frequency range, respectively.

The data output unit 23C generates, as output data OUT, a condition for acquiring the pulse wave data estimated to have high reliability from the RGB signal. In the present embodiment, the data output unit 23C generates a separation matrix for acquiring pulse wave data estimated to have high reliability from the RGB signal.

Specifically, as predetermined statistical processing for a separation matrix set according to each extraction condition, the data output unit 23C weights the separation matrix with the S/N ratio (value related to the quality of the analysis result) acquired under each extraction condition to generate a new separation matrix. In this case, the data output unit 23C generates a new separation matrix according to the following expression:

Output data OUT (new separation matrix)=(ICA1× SN1+ICA2×SN2+ . . . +ICA10×SN10)/(SN1+ SN2+ . . . +SN10)

In the above expression, the separation matrices set according to the respective extraction conditions C1 to C10 are represented as ICA1, ICA2, ICA10, respectively. Further, the S/N ratios acquired under the respective extraction conditions C1 to C10 are represented as SN1, SN2, . . . , SN10, respectively.

Thereby, the data output unit 23C can generate a new separation matrix estimated to have high reliability by weighting the separation matrix using the S/N ratio of the analysis target candidate data estimated to have high reliability among the analysis target candidate data acquired under each extraction condition. Since the data output unit 23C outputs the new separation matrix as the output data OUT, it becomes possible to apply the new separation matrix to the input data at the output destination, for example. Therefore, at the output destination, it is possible to acquire the pulse wave data estimated to have high reliability from the input data.

Note that, as described in Embodiments 2 and 3, the extraction conditions of the present embodiment are set so that the extracted data having a continuous set of the primary characteristic value and the secondary characteristic value can be extracted. Therefore, the data analysis device 1C can acquire the analysis target candidate data having a desired waveform and can calculate the S/N ratio thereof. In the present embodiment, as described above, each extraction condition is set so that the set of the primary characteristic value and the secondary characteristic value can be extracted every 10 frames of the input data. Further, as described above, in each extraction condition, the number of primary characteristic values to be extracted is the same.

Whether or not the analysis target candidate data having a desired waveform can be acquired is also influenced by the number of images acquired by the camera 10 per unit time. For example, when the input data is moving image data imaged by the camera 10 with 100 fps (frames per second), since the extracted data includes 10 sets of a primary characteristic value and a secondary characteristic value per second, a clear waveform can be acquired. On the other hand, when the input data is moving image data imaged by the camera 10 with 30 fps, the extracted data includes only three sets of a primary characteristic value and a secondary characteristic value per second, and it is difficult to acquire a clear waveform. In this way, in the present embodiment, in order to acquire a desired waveform, the number of images per unit time acquired by the camera 10 is also set in addition to the extraction condition setting.

Modification Example

The data output unit 23C only needs to be able to output a separation matrix or analysis target candidate data estimated to have high reliability. For example, as predetermined statistical processing for the separation matrices set for the extraction conditions, the data output unit 23C may generate an average of the separation matrices as a new separation matrix.

In this case, the data identification unit 22C identifies the separation matrices set for the extraction conditions as the analysis target data. That is, the data identification unit 22C identifies, as analysis target data, an analysis condition (for example, separation matrix) used when a plurality of pieces of analysis target candidate data are acquired by performing predetermined analysis processing (for example, independent component analysis) on the plurality of pieces of extracted data for each of the plurality of extraction conditions. In this case, the extraction conditions can be randomly set.

Further, the data analysis device 1C may generate pulse wave data estimated to have high reliability by applying the new separation matrix generated by the data output unit 23C to the set of input data.

Effect

The data analysis device 1C can increase the possibility of extracting pulse wave data less affected by a variation factor. In addition, the data analysis device 1C generates an analysis condition estimated to have high reliability. Therefore, the data analysis device 1C or the output destination can perform analysis processing on the input data using the analysis condition. That is, the data analysis device 1C or the output destination can accurately extract the data less affected by the variation factor from the input data.

Embodiment 5

In Embodiments 1 to 4, the set of input data input to the data analysis devices 1, 1A to 1C is one. The present embodiment differs from the data analysis devices 1, 1A to 1C in that there are a plurality of sets of input data input to data analysis devices 1D and 1E.

<Data Analysis Device>

Figure 15:
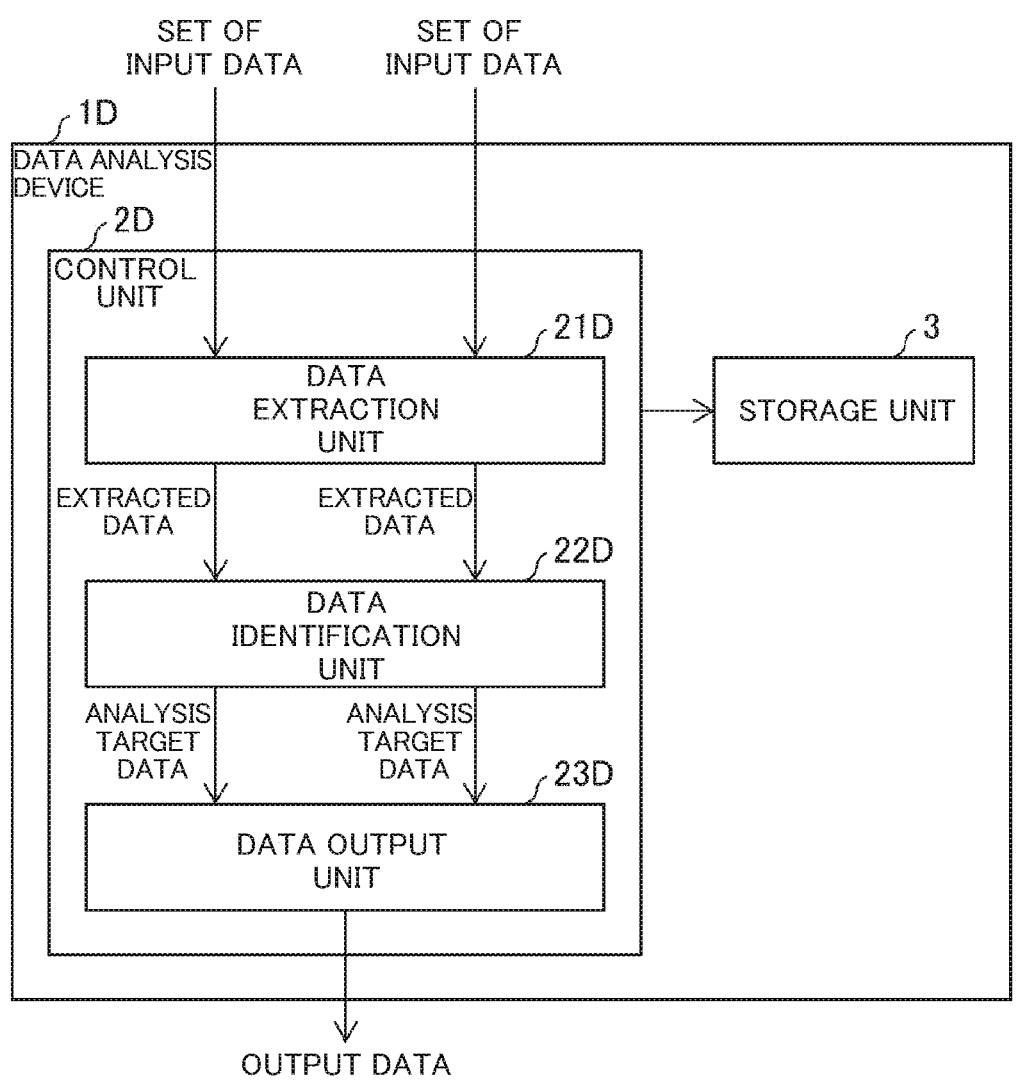
FIG. 15 is a block diagram showing an example of a data analysis device according to Embodiment 5.

FIG. 15 is a block diagram showing an example of a data analysis device 1D. As shown in FIG. 15, the data analysis device 1D includes a control unit 2D and the storage unit 3. The control unit 2D includes a data extraction unit 21D, a data identification unit 22D, and a data output unit 23D. The data extraction unit 21D, the data identification unit 22D, and the data output unit 23D have the functions similar to the data extraction unit 21, the data identification unit 22, and the data output unit 23 of the control unit 2 of Embodiment 1, but differ in the following points.

The data extraction unit 21D extracts, as extracted data, a plurality of sets of a primary characteristic value and a secondary characteristic value according to a plurality of extraction conditions different from each other, for each of a plurality of sets of input data.

As in Embodiment 1, the data identification unit 22D performs predetermined analysis processing on the plurality of pieces of extracted data for each of the plurality of extraction conditions, and identifies analysis target data on the basis of a result of the analysis processing. However, the identification processing is performed for each of a plurality of sets of input data.

The data output unit 23D executes randomly set processing on the analysis target data identified for each of the plurality of sets of input data. A specific example (data analysis device 1E) of the present embodiment will be described below.

<Processing in Data Analysis Device>

Figure 16:
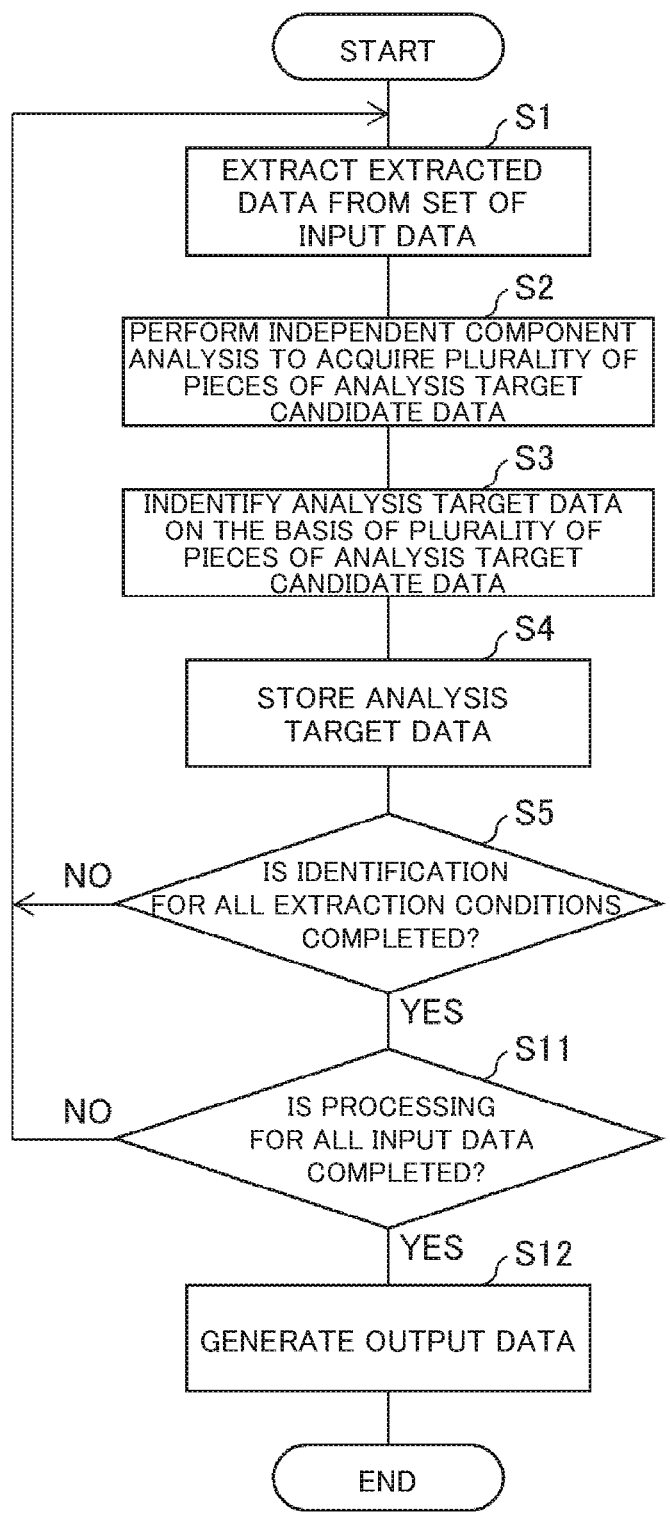
FIG. 16 is a flowchart showing an example of processing in the data analysis device.

FIG. 16 is a flowchart showing an example of processing in the data analysis device 1D. As shown in FIG. 16, the data analysis device 1D performs the processing of S1 to S5 described in Embodiment 1 on any set of input data. When the data extraction unit 21D determines that the analysis target data is identified for each of all the extraction conditions (YES in S5), the data extraction unit 21D determines whether or not the processing of S1 to S5 is performed on all the sets of input data (S11). When the data extraction unit 21D determines that the processing of S1 to S5 is not performed on all the sets of input data (NO in S11), the processing of S1 to S5 is performed until the analysis target data is identified for all the sets of input data. On the other hand, when the data extraction unit 21D determines that the processing of S1 to S5 is performed on all the sets of input data (YES in S11), the data output unit 23D generates output data on the basis of all the analysis target data in all the sets of input data (S12).

The processing of S1 to S5 may be executed in parallel for each set of input data.

Example

Figure 17:
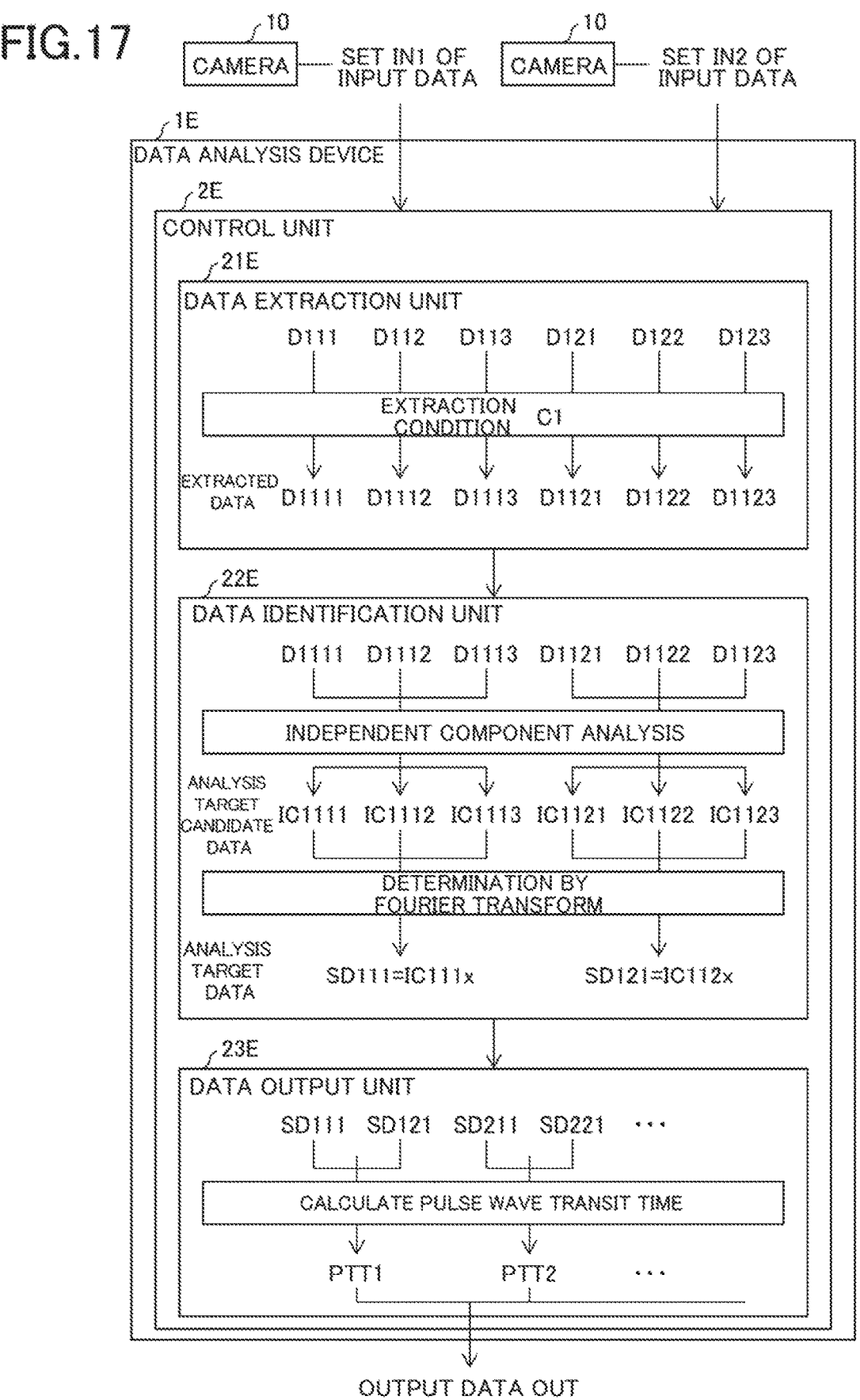
FIG. 17 is a block diagram showing an example of a data analysis device according to an example of Embodiment 5.

FIG. 17 is a block diagram showing an example of a data analysis device 1E. The data analysis device 1E is one of the examples of the data analysis device 1D. The data analysis device 1E calculates a pulse wave transit time estimated to have high reliability by using pulse wave data acquired from each of a plurality of RGB signals. As shown in FIG. 17, the data analysis device 1E includes a control unit 2E and the storage unit 3 (not shown). The control unit 2E includes a data extraction unit 21E, a data identification unit 22E, and a data output unit 23E. Since the data analysis device 1E is an example of the data analysis device 1D, the data extraction unit 21E, the data identification unit 22E, and the data output unit 23E have the same functions as the data extraction unit 21D, the data identification unit 22D, and the data output unit 23D.

In this example, sets IN1 and IN2 of input data that are extraction sources of the data extraction unit 21E are RGB signals that form moving image data acquired by the two cameras 10 that image different parts of the living body. In this example, the case where there are two sets of input data (the case where the RGB signals are detected at two parts of the living body) is shown, but the number of sets of input data may be three or more. In this case, the set of input data is acquired by three or more cameras 10 that image different parts of the living body.

As the extraction condition, for example, any of the extraction conditions of Embodiments 2 to 4 may be set. That is, it is sufficient that the extraction condition be set so that the analysis target candidate data having the waveform as the pulse wave data can be acquired as the analysis target data for calculating the pulse wave transit time. However, the data analysis device 1E calculates the pulse wave transit time using the analysis target data identified under each extraction condition in each of the sets IN1 and IN2 of input data. Therefore, all the extraction conditions used in each of the sets IN1 and IN2 of input data are the same. That is, the same extraction condition is used for a plurality of sets of input data.

The data extraction unit 21E extracts extracted data D1111, D1112, and D1113 from an R signal D111, a G signal D112, and a B signal D113 forming the set IN1 of input data, respectively, according to the extraction condition C1. The data identification unit 22E performs predetermined separation processing (for example, an independent component analysis (applying a separation matrix ICA1)) on the extracted data D1111, D1112, and D1113 to acquire analysis target candidate data IC1111, IC1112, and IC1113.

The data identification unit 22E selects analysis target candidate data estimated to have highest reliability as pulse wave data from the analysis target candidate data IC1111, IC1112, and IC1113. The data identification unit 22E executes, for example, a Fourier transform on each of the analysis target candidate data IC1111, IC1112, and IC1113. Then, from the analysis target candidate data IC1111, IC1112, and IC1113 after the Fourier transform, analysis target candidate data IC111$x$ having the highest signal strength in a predetermined frequency range (for example, 0.75 Hz or more and 4 Hz or less) is identified as analysis target data SD111.

The data extraction unit 21E and the data identification unit 22E also perform the same processing as the processing on the extraction condition C1 for the extraction conditions C2, C3, . . . to generate analysis target data SD211, SD311, . . . respectively corresponding to the extraction conditions C2, C3, . . . . Similar to the analysis target data SD111, the analysis target data SD211, SD311, . . . include analysis target candidate data IC121$x$, IC131$x$, . . . having the highest signal strength in a predetermined frequency range, respectively.

Further, the data extraction unit 21E and the data identification unit 22E perform the same processing as the processing on the set IN1 of input data for the set IN2 of input data configured by an R signal D121, a G signal D122, and a B signal D123. That is, the data extraction unit 21E extracts extracted data D1121, D1122, and D1123 from the R signal D121, the G signal D122, and the B signal D123 according to the extraction condition C1. The data identification unit 22E performs independent component analysis on the extracted data D1121, D1122, and D1123 to acquire analysis target candidate data IC1121, IC1122, and IC1123. Then, analysis target candidate data IC112$x$ is identified as analysis target data SD121. The data extraction unit 21E and the data identification unit 22E also perform similar processing on each of the extraction conditions C2, C3, . . . to generate analysis target data SD221, SD321, . . . corresponding to the extraction conditions C2, C3, . . . .

The data output unit 23E calculates a pulse wave transit time PPT$x$ on the basis of the analysis target data SD111, SD211, . . . acquired from the set IN1 of input data and the analysis target data SD121, SD221, . . . acquired from the set IN2 of input data.

For example, the data output unit 23E identifies a peak position in the waveform of the analysis target data SD111 acquired from the set IN1 of input data and a peak position in the waveform of the analysis target data SD121 acquired from the set IN2 of input data under the extraction condition C1. The data output unit 23E calculates a time difference between the two identified peak positions as a pulse wave transit time PPT1 under the extraction condition C1. The data output unit 23E calculates pulse wave transit times PPT2, PPT3, . . . for each of the extraction conditions C2, C3, . . . as in the case of the extraction condition C1.

The data output unit 23E outputs data including the calculated pulse wave transit times PPT1, PPT2, PPT3, . . . as output data OUT. The pulse wave transit times PPT1, PPT2, PPT3, . . . are calculated using data (analysis target data) estimated to be pulse wave data under each extraction condition. Since the extraction conditions are different from each other, the analysis target data also includes accurate pulse wave data. Therefore, it is possible to provide the output destination with (accurate) pulse wave transit time less affected by a variation factor.

Modification Example

The sets IN1 and IN2 of input data may be obtained by extracting the RGB signals of portions in which different parts of the living body are imaged from the RGB signals forming the moving image data acquired by the one camera 10. Even when there are three or more sets of input data, a plurality of sets of input data may be acquired from the RGB signals forming the moving image data acquired by the one camera 10.

Further, the calculated pulse wave transit time does not necessarily have to be used as output data OUT as it is. The data analysis device 1E may generate the output data OUT based on the calculated pulse wave transit time, as in Embodiment 2 or 4.

As in Embodiment 2, the data analysis device 1E may determine the reliability of the calculated pulse wave transit time. In this case, the data output unit 23E selects any two from the pulse wave transit times PPT1, PPT2, PPT3, . . . and calculates an error between the two pulse wave transit times by taking a difference between them. This processing is performed for all the pulse wave transit times PPT1, PPT2, PPT3, . . . .

When there is an error whose maximum value is equal to or greater than a predetermined value among the calculated errors, the data output unit 23E determines that the reliability of the pulse wave transit times PPT1, PPT2, PPT3, . . . is low. On the other hand, when the maximum value of the calculated errors is less than the predetermined value, the data output unit 23E determines that the reliability of the pulse wave transit times PPT1, PPT2, PPT3, . . . is high. The data output unit 23E outputs this determination result as the output data OUT.

Further, as in Embodiment 4, processing for extracting the pulse wave transit time estimated to have high reliability may be performed. In this case, the data identification unit 22E identifies the separation matrices ICA1, ICA2, . . . respectively corresponding to the extraction conditions C1, C2, . . . as the analysis target data SD111, SD211, . . . for the set IN1 of input data. Further, the data identification unit 22E identifies the respective S/N ratios of the analysis target candidate data IC111$x$, IC121$x$, . . . as the analysis target data SD111, SD211, . . . .

When the analysis target data SD111, SD211, . . . are identified, as described in Embodiment 4, the data output unit 23E weights the separation matrices ICA1, ICA2, . . . with the corresponding S/N ratios to calculate a new separation matrix.

The data identification unit 22E and the data output unit 23E also perform the same processing as the processing on the set IN1 of input data for the set IN2 of input data. The data identification unit 22E identifies the separation matrices ICA1, ICA2, . . . respectively corresponding to the extraction conditions C1, C2, . . . as the analysis target data SD121, SD221, . . . . Further, the data identification unit 22E identifies the respective S/N ratios of the analysis target candidate data IC112$x$, IC122$x$, . . . as the analysis target data SD121, SD221, . . . . The data output unit 23E weights the separation matrices ICA1, ICA2, . . . with the corresponding S/N ratios to calculate a new separation matrix.

The data output unit 23E applies the generated new separation matrix to each of the sets IN1 and IN2 of input data to acquire analysis target candidate data. The data output unit 23E calculates a time difference between the analysis target candidate data (for example, a time difference between peak positions of the analysis target candidate data) as pulse wave transit time, and outputs the pulse wave transit time as the output data OUT.

In this case, since the pulse wave transit time is calculated using a new separation matrix estimated to have high reliability, it can be estimated that the pulse wave transit time also has high reliability.

Effect

Similar to the data analysis device 1, the data analysis device 1D can increase the possibility of extracting a signal less affected by a variation factor from a plurality of sets of input data. For example, the data analysis device 1E can increase the possibility of extracting pulse wave data less affected by a variation factor from the RGB signals acquired from a plurality of parts of the living body. Therefore, the data analysis device 1E can generate an accurate pulse wave transit time.

Embodiment 6

Figure 18:
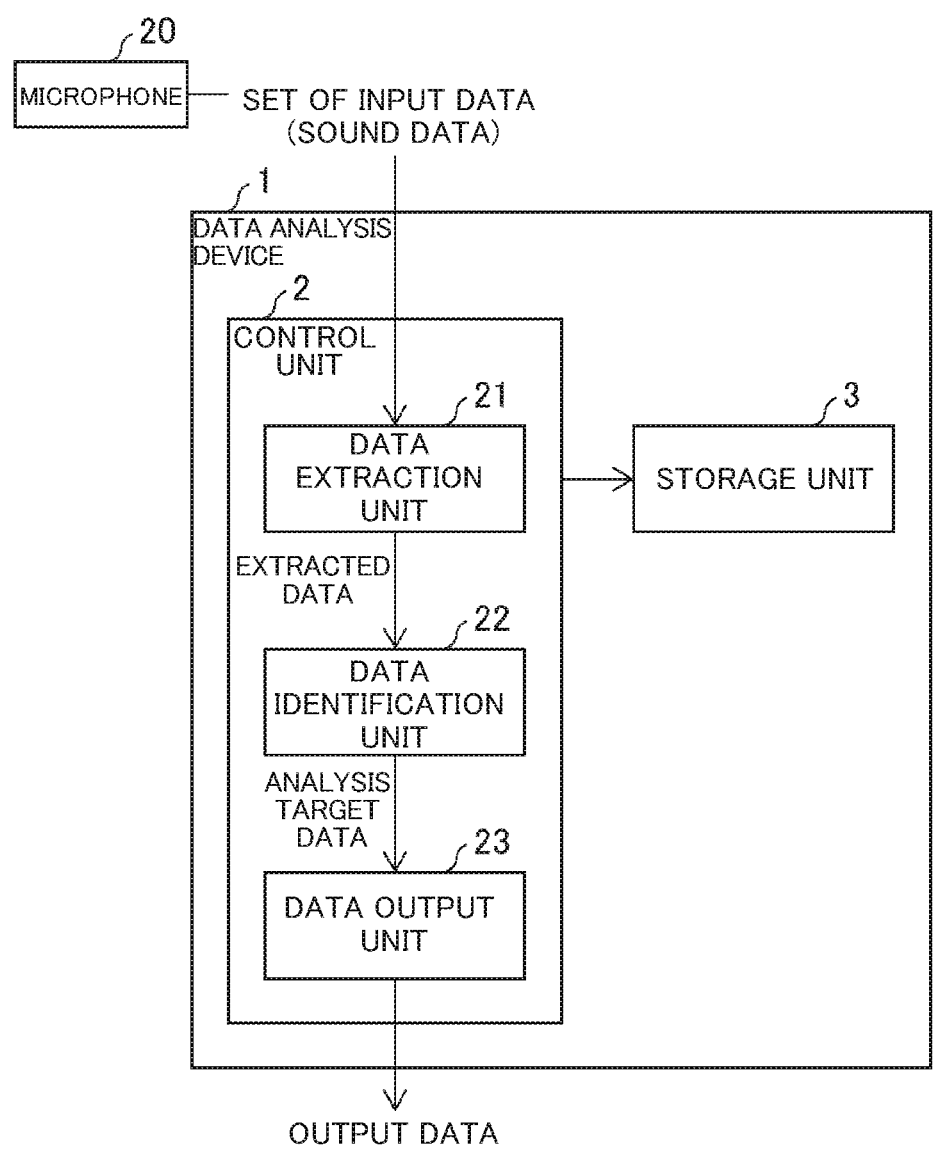
FIG. 18 is a block diagram showing an example of a data analysis device according to Embodiment 6.

FIG. 18 is a block diagram showing a modification example of the data analysis device 1. As shown in FIG. 18, the data analysis device 1 acquires input data as sound data from a microphone 20 having a sound collecting function. That is, in the present embodiment, the input data is sound data collected by the microphone 20.

The sound data may be, for example, voice data of a living body. That is, it can be said that biological information acquired from the living body is a voice. In this case, the voice data having a clear waveform can be accurately acquired.

However, the sound data collected by the microphone 20 does not have to be voice data of a living body, and may be, for example, environmental sound data (for example, noise data). In this case, the sound data having a clear waveform can be accurately acquired.

Embodiment 7

In the examples of Embodiments 2 to 4 and Embodiment 5, the set of input data has been described as being the RGB signal forming the moving image data of the living body imaged by the camera 10, but the present disclosure is not limited thereto. The RGB signal acquired from the living body may be acquired by, for example, a contact type or non-contact type sensor instead of the camera 10. In this case, the RGB signal can also be acquired by the sensor. That is, the RGB signal does not have to be acquired from the moving image data.

In addition, in the examples of Embodiments 2 to 4 and Embodiment 5, it has been described that the input data includes the biological information acquired from the living body, and the biological information is the pulse wave (that is, the analysis target data is the pulse wave data). In this way, even when the input data includes the pulse wave as the biological information, the desired effect as described above can be obtained. The same applies to biological information other than the pulse wave.

However, the biological information does not have to be a pulse wave. The biological information may be any information acquired from the living body, which is a measurement source of the state of the living body (for example, heart rate, pulse rate, heartbeat interval, or stress level), and may be, for example, the voice data described in Embodiment 6 or a specific component included in the living body. Further, when information indicating the state of the living body can be directly acquired from the living body, the information may be biological information.

Further, as described in Embodiment 1, the input data may not include biological information. That is, the analysis target candidate data may be information other than biological information.

Further, as described in Embodiment 1, the primary attribute may be one other than the "time". That is, the input data may be data other than the time-series data. Further, in the examples of Embodiments 2 to 4 and Embodiment 5, the time-series data for 60 seconds is used as the input data, but the time-series data may be set to a length sufficient to acquire the analysis target data estimated to have high reliability.

Implementation Example by Software

The control blocks (in particular, the control units 2, 2A to 2E) of the data analysis devices 1, 1A to 1E may be implemented by a logic circuit (hardware) formed on an integrated circuit (IC chip) or the like, or may be implemented by software.

In the latter case, the data analysis devices 1, 1A to 1E include a computer that executes instructions of a program that is software that implements each function. This computer includes, for example, at least one processor (control device) and at least one computer-readable recording medium that stores the program. Then, in the computer, the processor reads the program from the recording medium and executes the program to achieve the object of the present disclosure. As the processor, for example, a central processing unit (CPU) can be used. As the recording medium, a "non-transitory tangible medium" such as a read only memory (ROM), a tape, a disk, a card, a semiconductor memory, a programmable logic circuit, or the like can be used. Further, a random access memory (RAM) for expanding the program may be further provided. The program may be supplied to the computer via any transmission medium (communication network, broadcast wave, or the like) capable of transmitting the program. It is to be noted that one aspect of the present disclosure can also be implemented in the form of a data signal in which the program is embodied by electronic transmission and which is embedded in a carrier wave.

APPENDIX

The present disclosure is not limited to the embodiments described above, various modifications can be made within the scope of the claims, and embodiments obtained by appropriately combining the technical means disclosed in the different embodiments are also included in the technical scope of the present disclosure. Furthermore, new technical features can be formed by combining the technical means disclosed in each embodiment.

Another Expression of Present Disclosure

The data analysis device of the present disclosure can also be expressed as follows.
(1) A data analysis device that analyzes input data, a primary attribute and a plurality of secondary attributes being present, a characteristic value of the primary attribute being set as a primary characteristic value, a characteristic value of the secondary attribute being set as a secondary characteristic value corresponding to the primary characteristic value, the input data including the primary characteristic value and the secondary characteristic value of the plurality of secondary attributes,
in which the data analysis device includes:
an extraction device that sets extraction conditions based on the primary characteristic value, and extracts, as extracted data, a primary characteristic value corresponding to the set extraction condition and a secondary characteristic value corresponding to the primary characteristic value;
a separation device that separates desired information from the extracted data as separated data;
a memory device that stores the separated data according to the extraction condition; and
an output device that generates output data using the separated data for each extraction condition stored in the memory device, and
the extraction device changes and sets extraction conditions.
(2) In (1) above, the primary attribute may be a time.
(3) In (1) or (2) above, the input data may be data (color data) related to color information of a living body acquired by a contact type or non-contact type sensor.
(4) In (1) or (2) above, the input data may be a moving image acquired by a camera.
(5) In (4) above, the moving image may be a moving image of a living body.
(6) In (1) or (2) above, the input data may be a sound acquired by a microphone.
(7) In (6) above, the sound may be a voice of a living body.
(8) In any one of (1) to (3), (5), and (7) above, the desired information may be biological information.
(9) In (8) above, the biological information may be a pulse wave.
(10) In any one of (1) to (9) above, the separation device may separate desired information by an independent component analysis.
(11) In (1) above, an analysis target data may be data related to a predetermined analysis processing, and the output data may be a result of comparing a plurality of pieces of analysis target data identified for each of the extraction conditions.
(12) In (11) above, the plurality of extraction conditions may be set so that a specific primary characteristic value and a secondary characteristic value corresponding to the specific primary characteristic value are included in any of the extracted data, the analysis target data may be an analysis result of the predetermined analysis processing, and the output data may be a result of comparing the plurality of pieces of analysis target data identified for each of the plurality of extraction conditions.
(13) In (11) above, each of the plurality of extraction condition may be set so that the same extracted data is extracted, the analysis target data may be data related to the predetermined analysis processing and an analysis result of the predetermined analysis processing, and the output data may be generated from the data related to the predetermined analysis processing on the basis of a quality of the analysis result of the predetermined analysis processing included in the plurality of pieces of analysis target data identified for each of the plurality of extraction conditions.

CROSS-REFERENCE OF RELATED APPLICATIONS

This application claims priority to Japanese Patent Application 2018-082301 filed on Apr. 23, 2018, and the contents of which are entirely incorporated herein by reference.

The invention claimed is:
1. A data analysis device that performs an analysis on a set of input data in which a primary characteristic value that is a characteristic value of a primary attribute is associated with a secondary characteristic value that is a characteristic value of a secondary attribute, the secondary characteristic value corresponding to the primary characteristic value, the set of input data including a plurality of pieces of input data in which attributes of the secondary characteristic value corresponding to the primary characteristic value are different from each other, the data analysis device comprising:
a data extraction unit that extracts, as extracted data, a plurality of primary characteristic values corresponding to a plurality of extraction conditions which are different from each other and a plurality of secondary characteristic values corresponding to the plurality of primary characteristic values, for each of the plurality of pieces of input data;
a data identification unit that performs predetermined analysis processing on a plurality of pieces of the extracted data, and identifies, based on a result of the predetermined analysis processing, analysis target data to be analyzed; and
a data output unit that outputs output data generated based on a plurality of pieces of analysis target data identified for each of the plurality of extraction conditions,
wherein the plurality of extraction conditions is set so that the plurality of primary characteristic values included in a specific range and the plurality of secondary characteristic values corresponding to the plurality of primary characteristic values included in the specific range are included in each of the plurality of pieces of extracted data, the data identification unit includes, as the analysis target data, one of a plurality of analysis results obtained by performing the predetermined analysis processing, the data output unit further outputs, as the output data, a result of comparison between the plurality of pieces of analysis target data identified for each of the plurality of extraction conditions, and the plurality of extraction conditions comprises ranges of the primary characteristic values different from each other.

2. The data analysis device according to claim 1, wherein the data identification unit includes, as the analysis target data, an analysis condition used in the predetermined analysis processing.

3. The data analysis device according to claim 1, wherein the plurality of extraction conditions is set to have an identical number of the plurality of primary characteristic values and an identical extraction interval of the plurality of primary characteristic values in each of the plurality of pieces of extracted data, and the data identification unit further includes, as the analysis target data, a value calculated for one of a plurality of analysis results obtained by performing the predetermined analysis processing, the value being related to a quality of the analysis result.

4. The data analysis device according to claim 1, wherein the plurality of extraction conditions is set to have an identical number of the plurality of primary characteristic values and an identical extraction interval of the plurality of primary characteristic values in each of the plurality of pieces of extracted data, the data identification unit further includes, as the analysis target data, an analysis condition used in the predetermined analysis processing, and the data output unit further outputs, as the output data, a new analysis condition obtained as a result of performing predetermined statistical processing on the analysis condition, for the plurality of pieces of analysis target data identified for each of the plurality of extraction conditions.

5. The data analysis device according to claim 4, wherein the data identification unit further includes, as the analysis target data, a value calculated for one of a plurality of analysis results obtained by performing the predetermined analysis processing, the value being related to a quality of the analysis result, and the data output unit further outputs, as the output data, a new analysis condition obtained as a result of performing the predetermined statistical processing by further using the value related to the quality, for the plurality of pieces of analysis target data identified for each of the plurality of extraction conditions.

6. The data analysis device according to claim 1, wherein the primary attribute is a time.

7. The data analysis device according to claim 1, wherein the input data is moving image data acquired by a camera.

8. The data analysis device according to claim 7, wherein an image represented by the moving image data includes an image of a living body.

9. The data analysis device according to claim 1, wherein the input data is color data that indicates color of a skin of a living body, the color data being acquired by a contact type or non-contact type sensor.

10. The data analysis device according to claim 1, wherein the input data is sound data acquired by a microphone.

11. The data analysis device according to claim 10, wherein the sound data is voice data of a living body.

12. The data analysis device according to claim 1, wherein the output data is biological information.

13. The data analysis device according to claim 12, wherein the biological information is a pulse wave.

14. The data analysis device according to claim 1, wherein the predetermined analysis processing is processing of performing an independent component analysis.

15. A data analysis method for performing an analysis on a set of input data in which a primary characteristic value that is a characteristic value of a primary attribute is associated with a secondary characteristic value that is a characteristic value of a secondary attribute, the secondary characteristic value corresponding to the primary characteristic value, the set of input data including a plurality of pieces of input data in which attributes of the secondary characteristic value corresponding to the primary characteristic value are different from each other, the data analysis method comprising:

extracting, as extracted data, a plurality of primary characteristic values corresponding to a plurality of extraction conditions which are different from each other and a plurality of secondary characteristic values corresponding to the plurality of primary characteristic values, for each of the plurality of pieces of input data;

performing predetermined analysis processing on a plurality of pieces of the extracted data, and identifying, based on a result of the predetermined analysis processing, analysis target data to be analyzed; and outputting output data generated based on a plurality of pieces of analysis target data identified for each of the plurality of extraction conditions, wherein the plurality of extraction conditions is set so that the plurality of primary characteristic values included in a specific range and the plurality of secondary characteristic values corresponding to the plurality of primary characteristic values included in the specific range are included in each of the plurality of pieces of extracted data, one of a plurality of analysis results obtained by performing the predetermined analysis processing is included as the analysis target data, a result of comparison between the plurality of pieces of analysis target data identified for each of the plurality of extraction conditions is output as the output data, and the plurality of extraction conditions comprises ranges of the primary characteristic values different from each other.

16. A data analysis device that performs an analysis on a set of input data in which a primary characteristic value that is a characteristic value of a primary attribute is associated with a secondary characteristic value that is a characteristic value of a secondary attribute, the secondary characteristic value corresponding to the primary characteristic value, the set of input data including a plurality of pieces of input data in which attributes of the secondary characteristic value corresponding to the primary characteristic value are different from each other, the data analysis device comprising:

a data extraction unit that extracts, as extracted data, a plurality of primary characteristic values corresponding to a plurality of extraction conditions which are different from each other and a plurality of secondary characteristic values corresponding to the plurality of primary characteristic values, for each of the plurality of pieces of input data;

a data identification unit that performs predetermined analysis processing on a plurality of pieces of the extracted data, and identifies, based on a result of the predetermined analysis processing, analysis target data to be analyzed; and a data output unit that outputs output data generated based on a plurality of pieces of analysis target data identified for each of the plurality of extraction conditions, wherein the plurality of extraction conditions is set so that the plurality of primary characteristic values included in a specific range and the plurality of secondary characteristic values corresponding to the plurality of primary characteristic values included in the specific range are included in each of the plurality of pieces of extracted data, the data identification unit includes, as the analysis target data, one of a plurality of analysis results obtained by performing the predetermined analysis processing, the data output unit further outputs, as the output data, a result of comparison between the plurality of pieces of analysis target data identified for each of the plurality of extraction conditions, the input data is moving image data acquired, and the plurality of extraction conditions comprises several frames of moving image data different from each other.

* * * * *